(12) United States Patent
Inomata

(10) Patent No.: US 11,432,785 B2
(45) Date of Patent: Sep. 6, 2022

(54) X-RAY IMAGING APPARATUS

(71) Applicant: Shimadzu Corporation, Kyoto (JP)

(72) Inventor: Shuichi Inomata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 137 days.

(21) Appl. No.: 17/047,196

(22) PCT Filed: Jan. 17, 2019

(86) PCT No.: PCT/JP2019/001271
§ 371 (c)(1),
(2) Date: Oct. 13, 2020

(87) PCT Pub. No.: WO2019/198292
PCT Pub. Date: Oct. 17, 2019

(65) Prior Publication Data
US 2021/0121146 A1 Apr. 29, 2021

(30) Foreign Application Priority Data
Apr. 13, 2018 (JP) .............................. JP2018-077482

(51) Int. Cl.
*G01T 1/24* (2006.01)
*A61B 6/00* (2006.01)

(52) U.S. Cl.
CPC .............. *A61B 6/467* (2013.01); *A61B 6/461* (2013.01); *A61B 6/54* (2013.01)

(58) Field of Classification Search
CPC ........... A61B 6/467; A61B 6/461; A61B 6/54; A61B 6/465; A61B 6/468; A61B 6/586; A61B 6/5258
See application file for complete search history.

(56) References Cited

FOREIGN PATENT DOCUMENTS

| EP | 0984393 A2 * | 3/2000 | ............. H04N 5/325 |
|---|---|---|---|
| JP | 2012-135697 A | 7/2012 | |
| JP | 2015-322 A | 1/2015 | |

OTHER PUBLICATIONS

Notice of Reasons for Refusal for Japanese Application No. 2020-513072, dated Jun. 18, 2021.
Written Opinion for PCT application PCT/JP2019/001271 dated Mar. 12, 2019.
Notice of Reasons for Refusal for corresponding Japanese patent application No. JP2020-513072, dated Sep. 16, 2021 submitted with a machine translation.

* cited by examiner

*Primary Examiner* — Don K Wong
(74) *Attorney, Agent, or Firm* — Muir Patent Law, PLLC

(57) ABSTRACT

In order to perform a setting of whether or not an input of an imaging failure reason at the time of an imaging failure is necessary, a check box 8j on whether or not the input of the imaging failure reason is necessary is displayed on a screen. When an operation to input a check mark in the check box 8j is performed, it is set that the input of the imaging failure reason is necessary. When an operation to remove the check mark from the check box 8j is performed, it is set that the input of the imaging failure reason is unnecessary. When it is set that the input of the imaging failure reason is necessary, a screen for inputting the imaging failure reason is displayed. When it is set that the input of the imaging failure reason is unnecessary, a screen for inputting the imaging failure reason is skipped. As a result, when the input of the imaging failure reason is unnecessary, the input operation is automatically skipped, reducing the burden on the operator.

6 Claims, 11 Drawing Sheets

FIG. 5

| 8C | User Information Registration Screen |
|---|---|

- Login Name : [_____] — 8o
- Password : [_____] — 8p
- Password (Re-entry) : [_____] — 8q
- Group : [▼] — 8r
- User Attribution : [▼] — 8s
- Kanji : [_____] — 8t
- Roman Character : [_____] — 8u 8v — ☑ The imaging failure reason is input at the time of imaging failure

[ O K ]  [ Cancel ]

| 8c | User Information Registration Screen |
|---|---|

Login Name _____ 8o

Password _____ 8p

Password (Re-entry) _____ 8q

OK    Cancel

FIG. 13

| 8c | User Information Registration Screen |
|---|---|

User Attribution : [▼] — 8s

OK    Cancel

X-RAY IMAGING APPARATUS

TECHNICAL FIELD

The present invention relates to an X-ray imaging apparatus for performing X-ray imaging, and more particularly, to a technique for performing re-imaging.

BACKGROUND OF THE INVENTION

In an examination using an X-ray imaging apparatus, positioning (alignment) of a patient (subject) and X-ray imaging conditions (e.g., a tube voltage, a tube current, an irradiation time, etc.) are set according to the imaging site ordered by a doctor, and the X-ray imaging by X-ray irradiation or the X-ray image acquired by the X-ray imaging is confirmed.

In confirming the X-ray image, there sometimes occurs a case in which an X-ray image sufficient for making a diagnosis cannot be generated (hereinafter referred to as "imaging failure") due to the reasons, e.g., the incorrect positioning of the patient, the inappropriate X-ray imaging conditions, or the like. In this case, re-imaging is performed. The re-imaging due to such imaging failure has disadvantages, such as, e.g., giving extra exposure to a patient and extending the examination time by the re-imaging. Generally, an X-ray image first captured when this re-imaging occurred is distinguished as an "imaging failure image" and is removed from the target to be diagnosed in operation.

In this regard, an X-ray imaging apparatus has a setting registration function (see the "Imaging failure" button B in FIG. 16) for setting the collected X-ray image as an imaging failure image by the operation of the user (operator) as shown in FIG. 16. It is also provided with a sub-function for automatically excluding the imaging failure image from the transmission target to an image server or a printer.

As described above, re-imaging due to imaging failure has disadvantages, such as, e.g., excessive exposure to a patient and an extended examination time due to the re-imaging. For this reason, how to eliminate such imaging failure is a challenge for medical institutions performing X-ray examinations. As an effort to reduce imaging failures, efforts have been performed in which statistical analysis processing, such as, e.g., protocols (procedures) of past imaging failures, causes of occurrence, and incidence rates, is performed, and an administrator analyzes them and guides a technician to reduce the imaging failure incidence rate. Specifically, at the time of confirming the imaging failure, the imaging failure image is set (set the imaging failure) as an image of the imaging failure, and the reason (also called "imaging failure reason") is input (see, for example, Patent Document 1).

More specifically, on the X-ray imaging apparatus side, an interface is prepared for the imaging failure image as shown in FIG. 17. The interface is configured for the user (operator) to input the reason (imaging failure reason) that the user judges as an imaging failure, such as, e.g., "the positioning of the patient was wrong" (in FIG. 17, "Movement of patient") or "the X-ray imaging conditions were inappropriate" (in FIG. 17, the reason (imaging failure reason judged as imaging failure such as the "Imaging condition failure"). This allows the administrator to easily implement statistical analysis processing related to the imaging failure. Other than the above, the "Misregistration" in FIG. 17 is a position aberration of the positioning of the imaging system, such as, e.g., an X-ray tube and an X-ray detector. The "Marker position misalignment" in FIG. 17 is the overlapping of the marker on the diagnostic location.

PRIOR ART DOCUMENT

Patent Document

Patent Document 1: Japanese Patent No. 5539435

SUMMARY OF THE INVENTION

Problems to be Solved by the Invention

However, the conventional example having the above-described configuration has the following problems.

That is, in the setting of the imaging failure reason of the X-ray imaging apparatus, the operator of the apparatus is necessary to perform some operations to confirm/input the imaging failure reason, thereby incurring some burden on the operator.

The present invention has been made in view of the above-described circumstances. An object thereof is to provide an X-ray imaging apparatus capable of reducing the burden on the operator.

Means for Solving the Problem

As a result of intensive researches to solve the above-described problems, the inventor has acquired the following findings.

In a prior art, in order to prevent the omission of a setting of the imaging failure reason, it is necessary to provide a function, such as, e.g., a function of displaying an interface for automatically inputting an imaging failure reason at the time of the imaging failure registration and a function of displaying a warning message when there is an imaging failure image in which the imaging failure reason has not been registered at the time of completion of imaging (completion of examination). Actually, however, because of the following reasons, it has been found the finding that there are cases in which the necessity/unnecessity of inputting an imaging failure reason differs for each user (operator) who performed imaging, for each content (imaging protocol) of imaging, or for each examination (procedure) in which a series of imaging is collectively performed. Here, the procedure refers to a collection of a plurality of processing. In this specification, since the processing corresponds to imaging, the following explanation will be given by assuming that the "examination" which collectively captures a series of imaging and the "procedure' are synonymous with each other.

More specifically, in cases where both the imaging performed by a technician and the imaging performed by a doctor are performed in one examination (procedure), it is assumed that an input of the imaging failure reason is necessary when the user (operator) who performed the imaging of the imaging failure image is a technician. However, when the user (operator) who performed the imaging of the failure image is a doctor, it is assumed that it is unnecessary to input the imaging failure reason because the doctor does not perform statistical analysis processing on the imaging failure. As described above, there are cases in which statistical analysis processing on the imaging failure is unnecessary, depending on the operator. Here, it is assumed that the input of the imaging failure reason is necessary when the operator is a technician and the input of the imaging failure reason is unnecessary when the operator is a doctor, but it should be noted that this is one example of an operation in hospitals. As will be described later, in the case of an experienced technician, it may be assumed that the input of the imaging failure reason is unnecessary. Conversely, in the case of a doctor, it may be assumed that the input of the imaging failure reason is necessary.

Further, in cases where the content of the X-ray imaging is a chest, an abdomen, or extremities, the input of the imaging failure reason is necessary. However, there exits imaging with a large number of imaging failures and imaging with a smaller number of imaging failures (e.g., contrast imaging). In the case of imaging with less imaging failure, the imaging failure reason is limited to "the positioning of the patient was wrong" which is not subjected to statistical analysis processing. Consequently, the input of the imaging failure reason is unnecessary in this case. As described above, depending on the content of imaging, there exist cases in which statistical analysis processing related to an imaging failure is unnecessary.

Further, in cases where the procedure is "General imaging of hand", the input of the imaging failure reason is necessary. However, there are a procedure with high imaging failures and a procedure with low imaging failures. In cases where the procedure with low imaging failures is, for example, a "contrast examination of upper gastrointestinal tract", the imaging failure reason is limited to the "positioning of the patient was wrong" like the case with less imaging failures. The imaging failure reason is not subjected to statistical analysis processing. Consequently, the input of the imaging failure reason is unnecessary. Thus, depending on a procedure, there are cases in which statistical analysis processing on the imaging failure is unnecessary.

Based on such findings, the present invention has the following configuration.

That is, an X-ray imaging apparatus according to the present invention is an X-ray imaging apparatus for performing X-ray imaging. The X-ray imaging apparatus includes:

a necessity/unnecessity setting means configured to perform a setting of whether or not an input of an imaging failure reason at the time of an imaging failure is necessary, the imaging failure reason being a reason of a failure of imaging at the time of an imaging failure set as a failure of imaging; and a display controller configured to control such that a screen for inputting the imaging failure reason is displayed when it is set by the necessity/unnecessity setting means that the input of the imaging failure reason is necessary and that a screen for inputting the imaging failure reason is skipped when it is set by the necessity/unnecessity setting means that the input of the imaging failure reason is unnecessary.

Functions and Effects

According to the X-ray imaging apparatus of the present invention, the apparatus is provided with a necessity/unnecessity setting means configured to perform a setting of whether or not an input of an imaging failure reason is necessary at the time of imaging failure. Further, the apparatus is provided with a display controller configured to perform the following control. When it is set by the necessity/unnecessity setting means that the input of the imaging failure reason is necessary, the display controller controls such that a screen for inputting the imaging failure reason is displayed. When it is set by the necessity/unnecessity setting means that the input of the imaging failure reason is unnecessary, the display controller controls such that the screen for inputting the imaging failure reason is skipped. By providing the necessity/unnecessity setting means and the display controller described above, when the input of the imaging failure reason is unnecessary, the input operation of the imaging failure reason is automatically skipped. As a result, when the input of the imaging failure reason is unnecessary, it becomes unnecessary for the operator to perform an operation to cancel the input of the imaging failure reason or the like, which can reduce the burden on the operator.

According to an example (former example) of the X-ray imaging apparatus of the present invention, the apparatus is further provided with a necessity/unnecessity input means configured to input whether or not the input of the imaging failure reason is necessary. The display controller is configured to control such that a setting item on whether or not the input of the imaging failure reason is necessary is displayed on a screen. When it is input by the necessity/unnecessity input means that the input of the imaging failure reason is necessary at the setting item displayed on the screen, the necessity/unnecessity setting means sets that the input of the imaging failure reason is necessary. When it is input by the necessity/unnecessity input means that the input of the imaging failure reason is unnecessary at the setting item displayed on the screen, the necessity/unnecessity setting means sets that the input of the imaging failure reason is unnecessary.

According to an example (former example) of the X-ray imaging apparatus of the present invention, the apparatus is further provided with a necessity/unnecessity input means configured to input whether or not the input of the imaging failure reason is necessary. The display controller is configured to control such that a setting item on whether or not the input of the imaging failure reason is necessary is displayed on the screen. When it is input by the necessity/unnecessity input means that the input of the imaging failure reason is necessary at the setting item displayed on the screen, the necessity/unnecessity setting means sets that the input of the imaging failure reason is necessary. With this, when it is input by the necessity/unnecessity input means that the input of the imaging failure reason is necessary at the setting item displayed on the screen, a screen for inputting the imaging failure is displayed and the imaging failure reason is input on the screen. To the contrary, when it is input by the necessity/unnecessity input means that the input of the imaging failure reason is unnecessary at the setting item displayed on the screen, the necessity/unnecessity setting means sets that the input of the imaging failure reason is unnecessary. With this, when it is input by the necessity/unnecessity input means that the input of the imaging failure reason is unnecessary at the setting item, the screen for inputting the imaging failure is skipped. Therefore, when the input of the imaging failure reason is unnecessary, the input operation is automatically skipped.

According to an example (latter example) of the X-ray imaging apparatus of the present invention, the apparatus is further provided with an operating condition input means configured to input an operating condition. The necessity/unnecessity setting means performs the setting of whether or not the input of the imaging failure reason is necessary depending on the operating condition input by the operating condition input means. When it is set by the necessity/unnecessity setting means that the input of the imaging failure reason is unnecessary in a specific operating condition, the display controller controls such that the screen for performing the setting of whether or not the imaging failure reason is necessary is skipped in the specific operating condition.

In the latter example, there is provided an operating condition input means for inputting an operating condition. The necessity/unnecessity setting means performs the setting of whether or not the input of the imaging failure reason is necessary depending on the operating condition input by the operating condition input means. On the other hand, when it is set by the necessity/unnecessity setting means that the input of the imaging failure reason is unnecessary in the specific operating condition, the display controller controls such that the screen for inputting on whether or not the input of the imaging failure reason is necessary is skipped in the specific operating condition. As a result, when the input of the imaging failure reason is unnecessary in a particular operating condition, the screen for performing the setting of whether or not the input of the imaging failure reason is necessary is skipped. Therefore, the operation itself for inputting that the input of the input of the imaging failure reason is unnecessary is automatically skipped. As a result, when the input of the imaging failure reason is unnecessary in a specific operating condition, the operation for inputting the imaging failure reason, in addition to the operation for canceling the input of the imaging failure reason, can be avoided. Therefore, the burden on the operator can be further reduced.

In the latter example, as the operating condition input by the operating condition input means, there are the following first to third aspects.

According to the first aspect, the operating condition to be input by the operating condition input means is a content of an imaging protocol. The necessity/unnecessity setting means performs the setting of whether or not the input of the imaging failure reason is necessary depending on the content of each imaging protocol input by the operating condition input means. When it is set by the necessity/unnecessity setting means that the input of the imaging failure reason is unnecessary in a specific imaging protocol, the display controller controls such that the screen for performing the setting of whether or not the input of the imaging failure reason is necessary is skipped in the specific imaging protocol.

According to the first aspect, when it is set by the necessity/unnecessity setting means that the input of the imaging failure reason is unnecessary in a specific imaging protocol, the display controller controls such that the screen for performing a setting of whether or not the input of the imaging failure reason is necessary is skipped in the specific imaging protocol. As a result, when the input of the imaging failure reason is unnecessary in a particular imaging protocol, the screen on whether or not the input of the imaging failure reason is necessary is skipped. Therefore, the operation itself for inputting that the input of the imaging failure reason is unnecessary is automatically skipped. As a result, in the case of an imaging protocol in which the input of the imaging failure reason is unnecessary, the operation for inputting that the input of the imaging failure reason is unnecessary, in addition to the operation of canceling the input of the imaging failure reason, can be avoided. Therefore, the burden on the operator can be further reduced.

Further, according to the second aspect, which is different from the first aspect, the operating condition to be input by the operating condition input means is information of an operator. The necessity/unnecessity setting means performs the setting of whether or not the input of the imaging failure reason is necessary depending on the information of each operator input by the operating condition input means. When it is set by the necessity/unnecessity setting means that the input of the imaging failure reason is unnecessary in a case of a specific operator, the display controller controls such that the screen for performing the setting of whether or not the input of the imaging failure reason is necessary is skipped in the case of the specific operator.

According to the second aspect, when it is set by the necessity/unnecessity setting means that the input of the imaging failure reason is unnecessary in the case of the specific operator, the display controller controls such that the screen for performing the setting of whether or not the input of the imaging failure reason is necessary is skipped in the case of a specific operator. As a result, when the input of the imaging failure reason is unnecessary in the case of a particular operator, the screen for performing the setting of whether or not the input of the imaging failure reason is necessary is skipped. Therefore, the operation itself of inputting that the input of the imaging failure reason is unnecessary is automatically skipped. As a result, in the case of an operator that the input of the imaging failure reason is unnecessary (for example, a doctor or an experienced technician), in addition to the operation of canceling the input of the imaging failure reason, the operation of inputting that the input of the imaging failure reason is unnecessary can be avoided. Therefore, the burden on the operator can be further reduced.

Further, according to the third aspect, which is different from the first and second aspects, the operating condition to be input by the operating condition input means is a content of a procedure in which a series of imaging is collectively performed. The necessity/unnecessity setting means performs the setting of whether or not the input of the imaging failure reason is necessary depending on a content of each procedure input by the operating condition input means. When it is set by the necessity/unnecessity setting means that the input of the imaging failure reason is unnecessary in a specific procedure, the display controller controls such that the screen for performing the setting of whether or not the input of the imaging failure reason is necessary is skipped in the specific procedure.

According to the third aspect, when it is set by the necessity/unnecessity setting means that the input of the imaging failure reason is unnecessary in a specific procedure, the display controller controls such that the screen for performing the setting of whether or not the input of the imaging failure reason is necessary is skipped in the specific procedure. With this, when the input of the imaging failure reason is unnecessary in a particular procedure, the screen for performing the setting of whether or not the input of the imaging failure reason is necessary is skipped. Therefore, the operation itself of inputting that the input of the imaging failure reason is unnecessary is automatically skipped. As a result, in the case of a procedure in which the input of the imaging failure reason is unnecessary, the operation of inputting that the input of the imaging failure reason can be avoided, in addition to the operation of canceling the input of the imaging failure reason. Therefore, the burden on the operator can be further reduced.

Effects of the Invention

According to the X-ray imaging apparatus of the present invention, the apparatus is provided with: a necessity/unnecessity setting means configured to perform a setting of whether or not an input of an imaging failure reason at the time of imaging failure is necessary; and a display controller configured to control such that a screen for inputting the imaging failure is displayed when it is set by the necessity/unnecessity setting means that the input of the imaging failure reason is necessary and that a screen for inputting the imaging failure reason is skipped when it is set by the necessity/unnecessity setting means that the input of the imaging failure reason is unnecessary. When the input of the imaging failure reason is unnecessary, the input operation is automatically skipped, thereby reducing the burden on the operator.

BRIEF DESCRIPTION OF THE DRAWINGS

FIG. 5 is a display mode of a user information registration screen according to Example 1.

Figure 3:
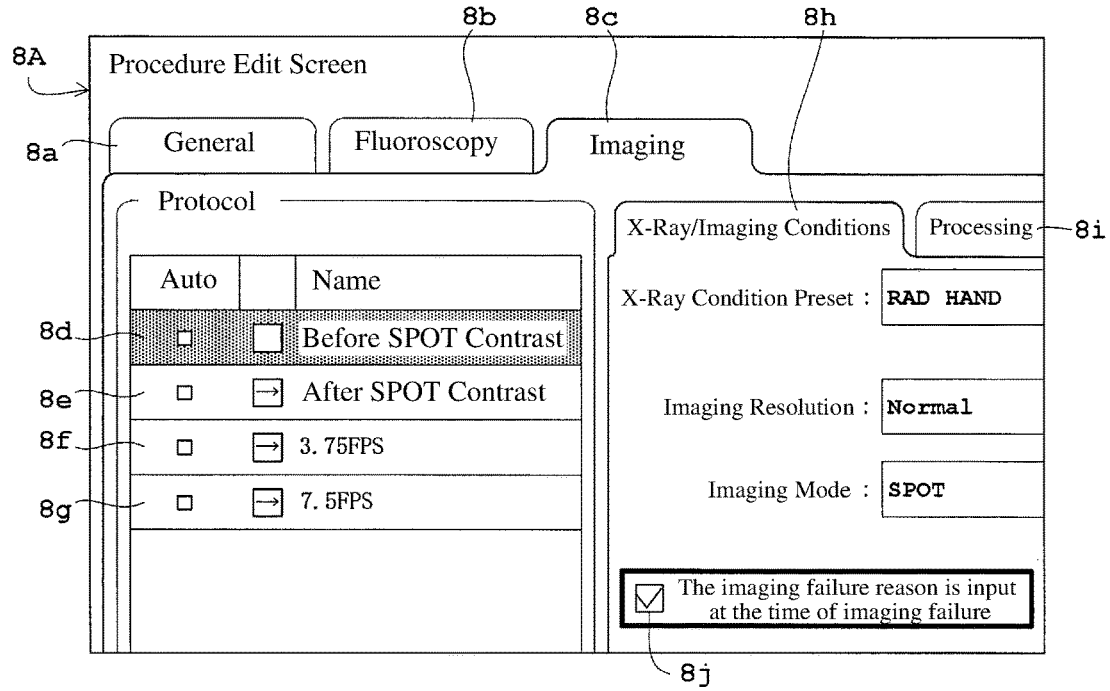
FIG. 3 is a display mode of a procedure edit screen according to Example 1.
Figure 6:
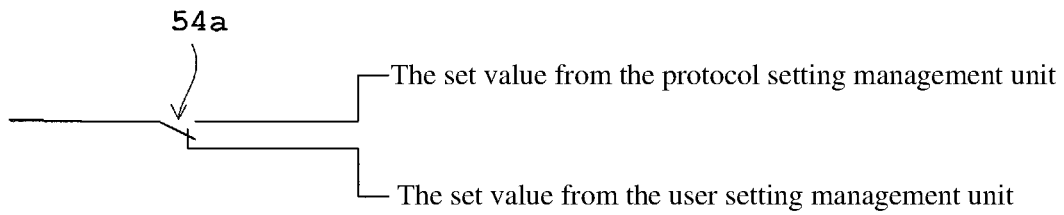
Figure 6:
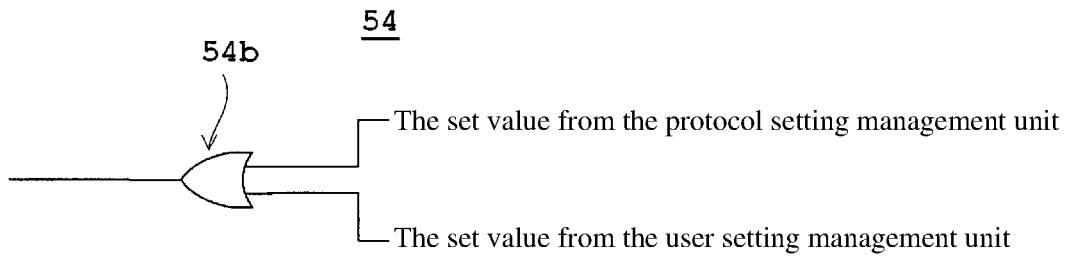
Figure 6:
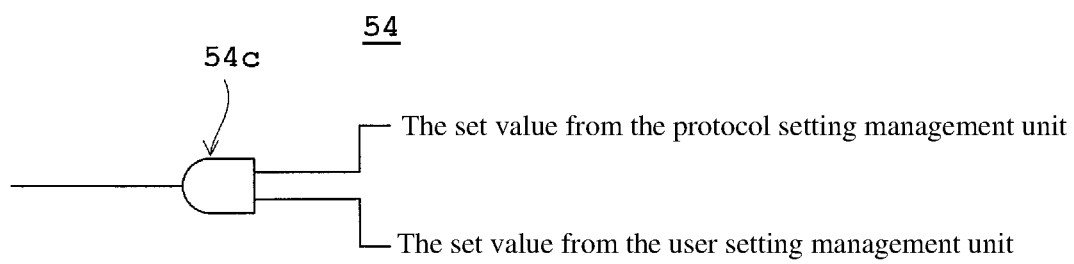

(a) to (c) of FIG. 6 each are a circuit diagram of an imaging failure reason determination unit when implemented by combining the display modes of FIG. 3 and FIG. 5.

Figure 7:
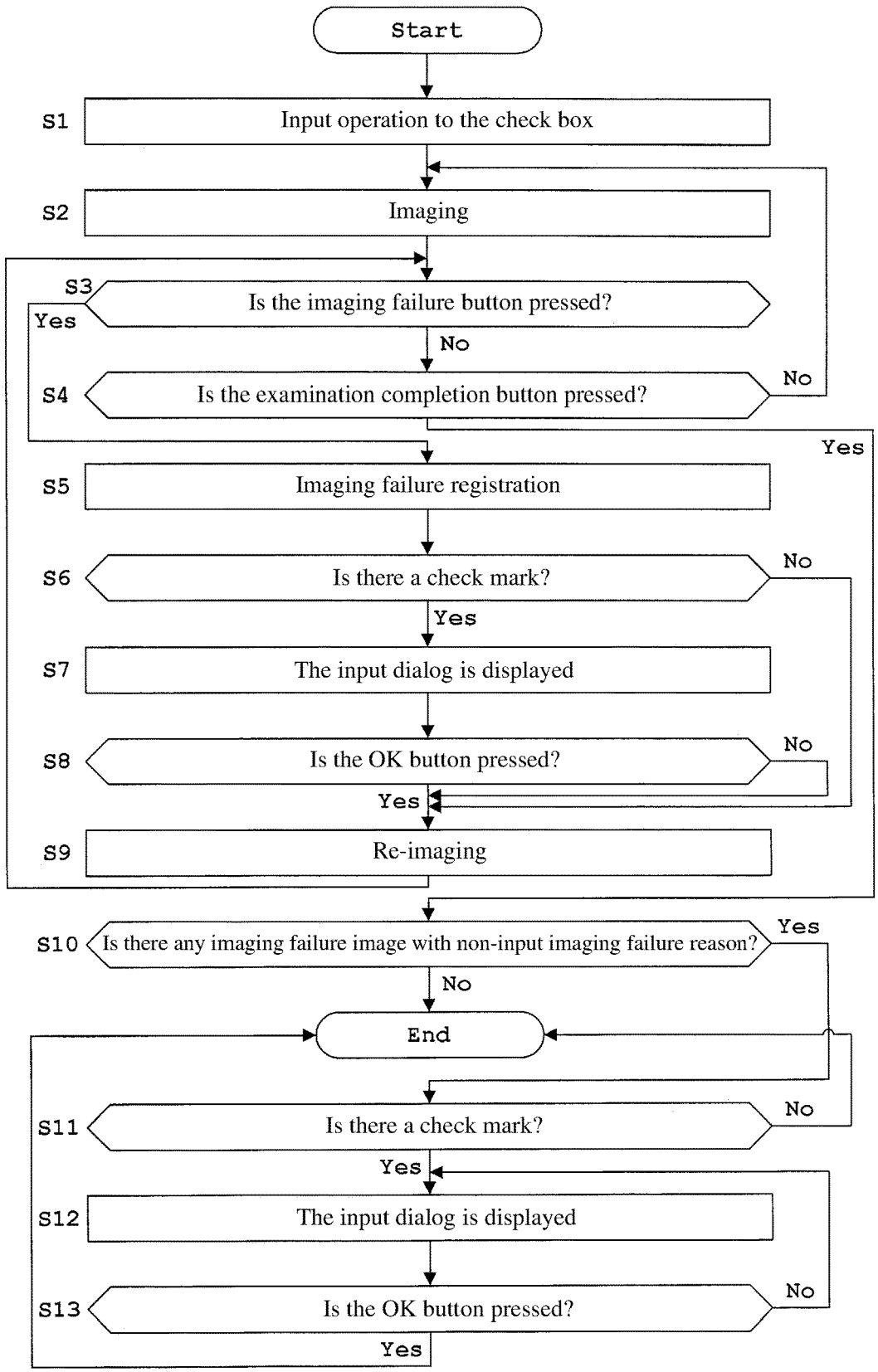

FIG. 7 is a flowchart of a series of imaging according to Example 1 including a setting of whether or not the input of the imaging failure reason is necessary.

Figure 8:
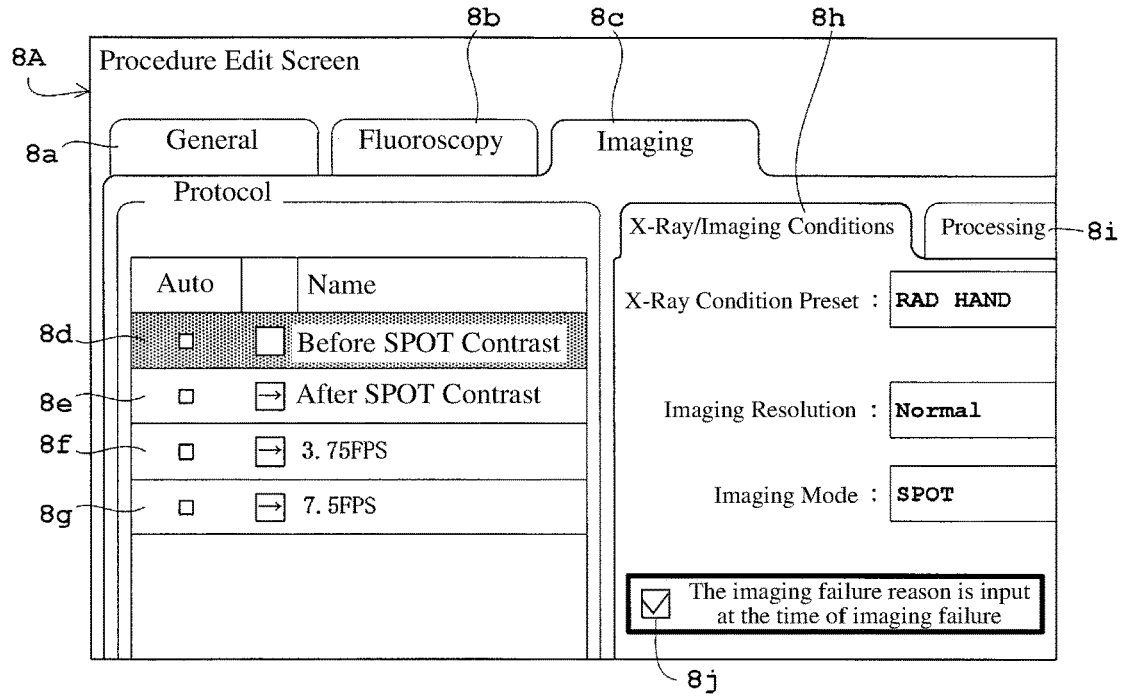

FIG. 8 is a display mode showing a procedure edit screen according to Example 2 when it is set that an input of the imaging failure reason is necessary in a particular imaging protocol.

Figure 9:
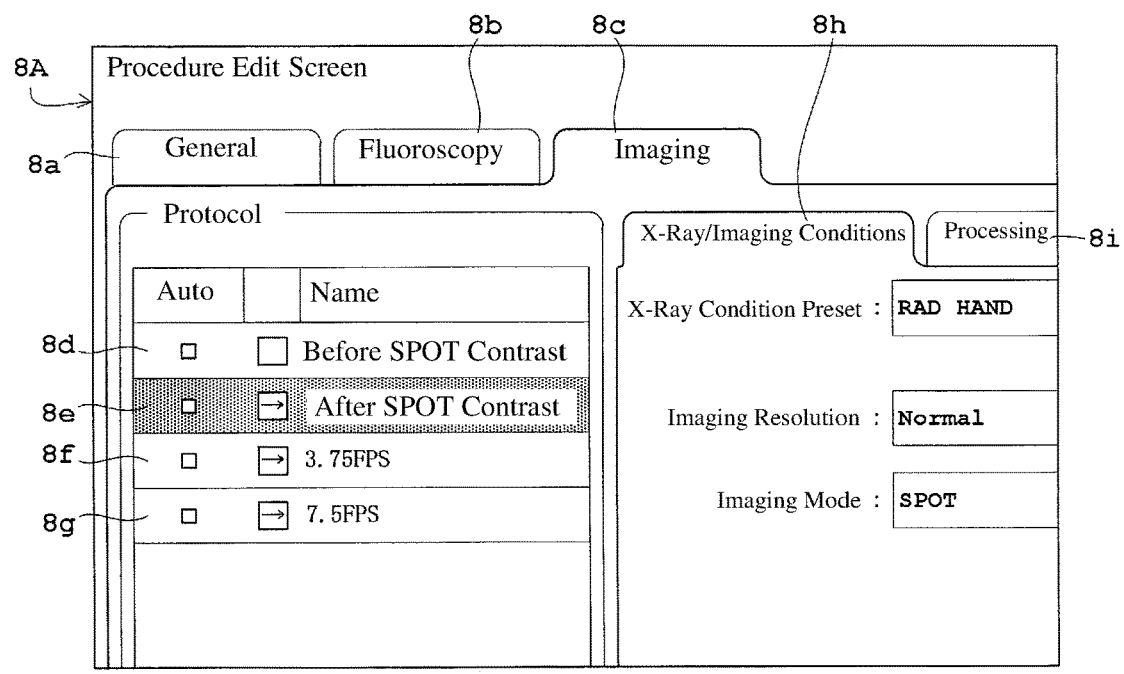

FIG. 9 is a display mode showing a procedure edit screen according to Example 2 when it is set that an input of the imaging failure reason is unnecessary in a particular imaging protocol.

Figure 10:
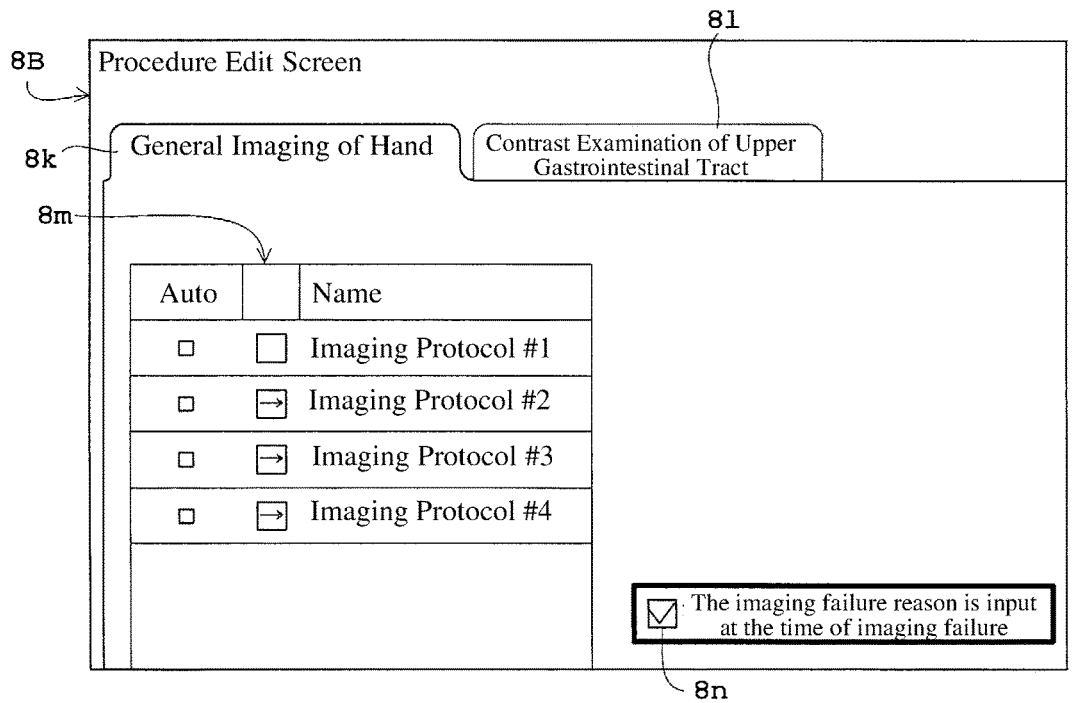

FIG. 10 is a display mode showing a procedure edit screen according to Example 2 when it is set that an input of the imaging failure reason is necessary in a particular procedure.

Figure 11:
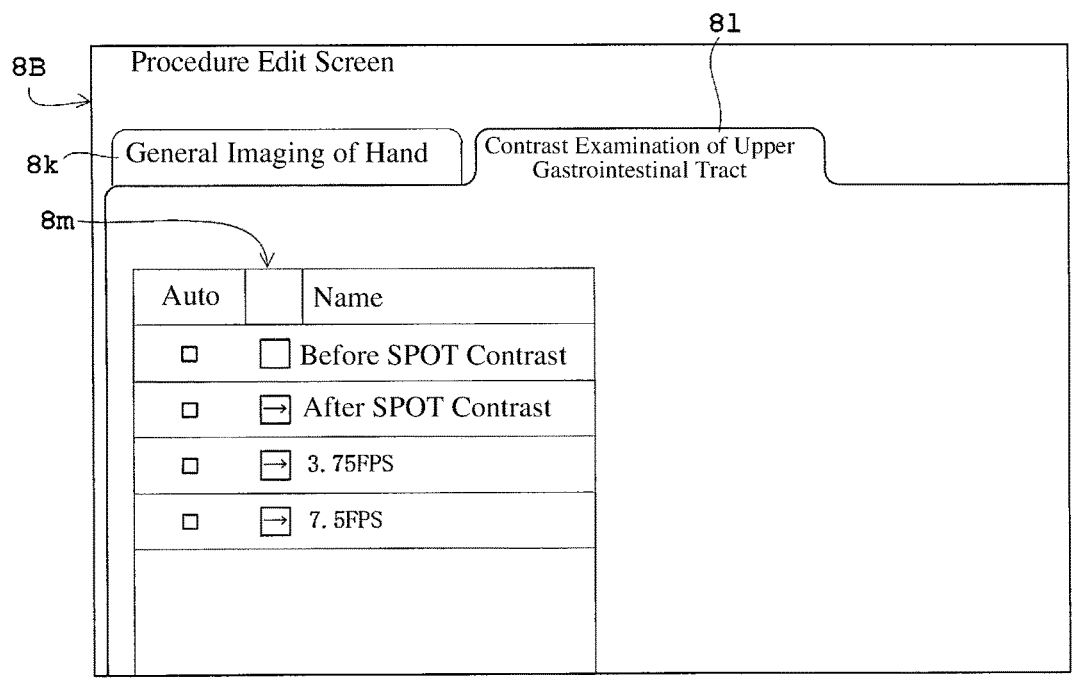

FIG. 11 is a display mode showing a procedure edit screen according to Example 2 when it is set that an input of the imaging failure reason is unnecessary in a particular procedure.

FIG. 12 is a display mode showing a user information registration screen of Example 2 prior to logging in.

FIG. 13 is a display mode showing a user information registration screen according to Example 2, which is a display mode different from FIG. 12.

Figure 14:
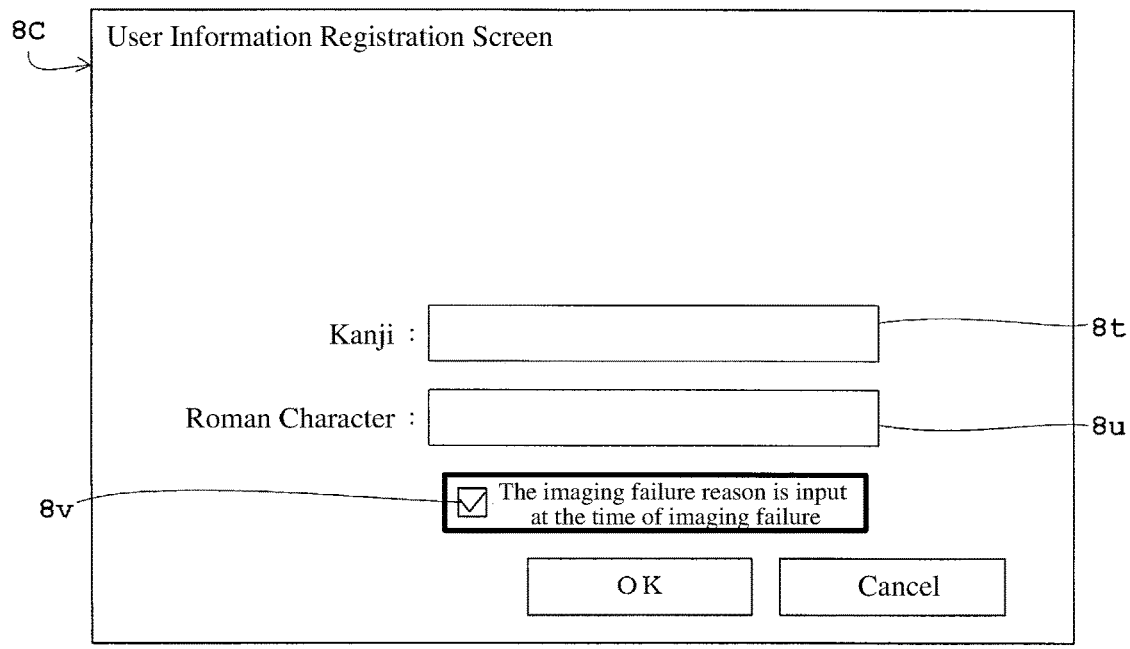

FIG. 14 is a display mode showing a user information registration screen according to Example 2 when it is set that an input of the imaging failure reason is necessary in the case of a particular operator.

Figure 15:
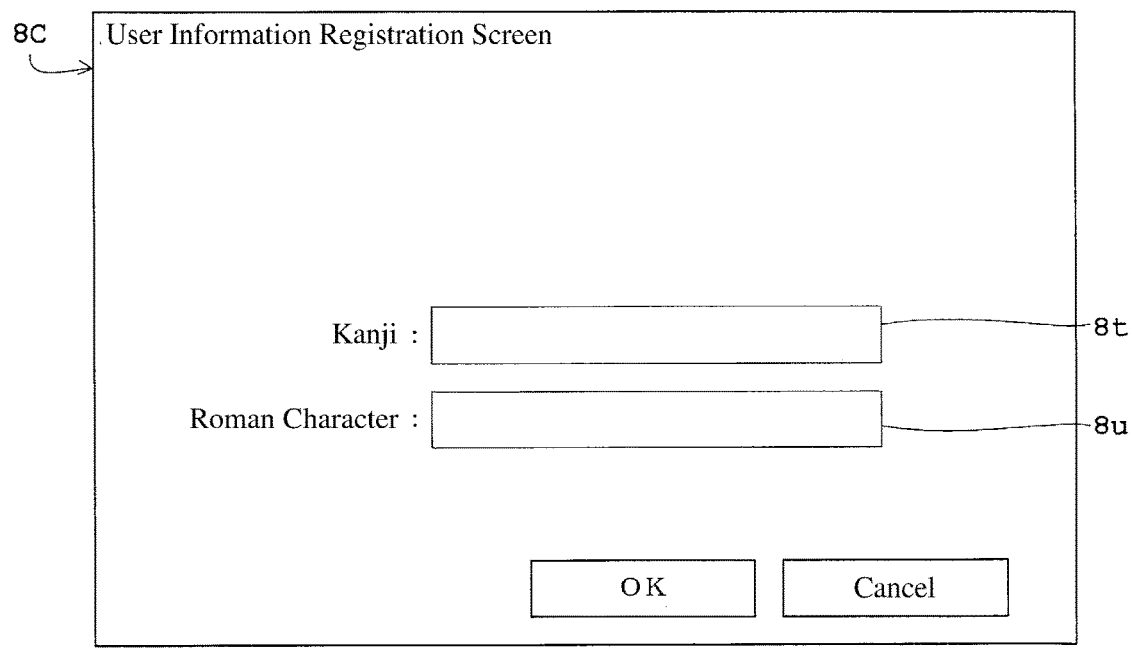

FIG. 15 is a display mode showing a user information registration screen according to Example 2 when it is set that an input of the imaging failure reason is unnecessary in the case of a particular operator.

Figure 16:
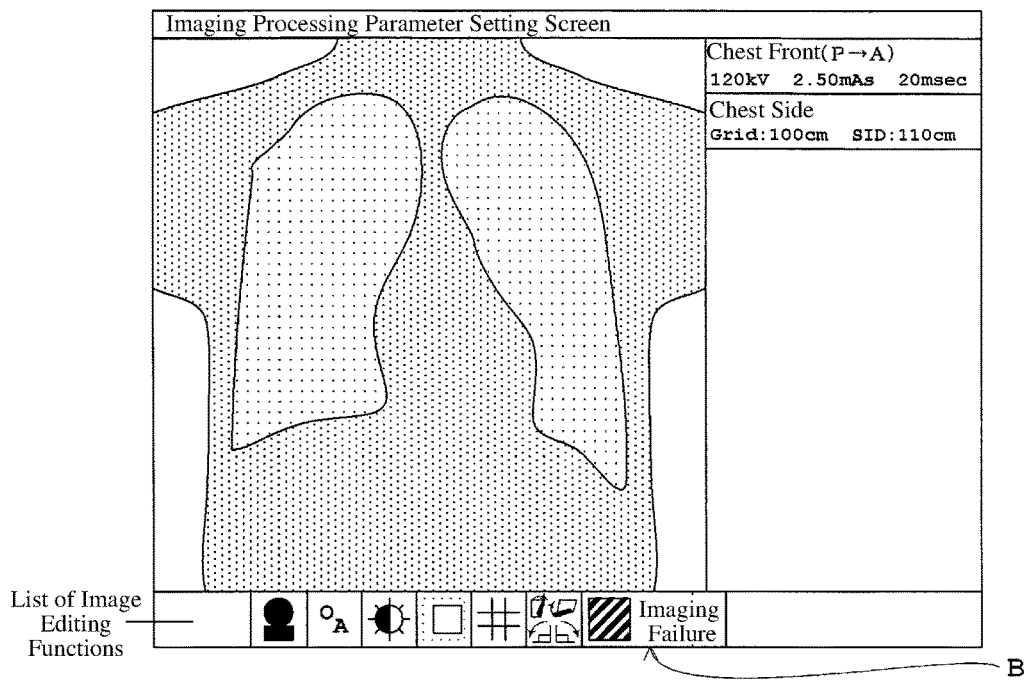

FIG. 16 is a display mode showing a screen provided with an imaging failure button for an imaging failure registration.

Figure 17:
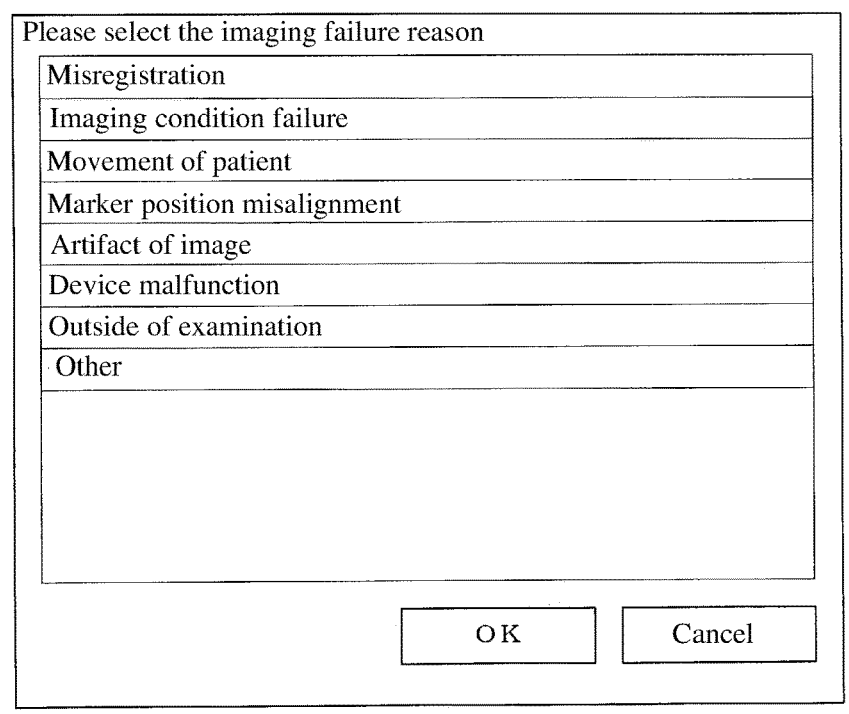

FIG. 17 is a display mode showing an input dialog of the imaging failure reason.

EXAMPLE 1

Hereinafter, Example 1 of the present invention will be described with reference to the attached drawings.

Figure 1:
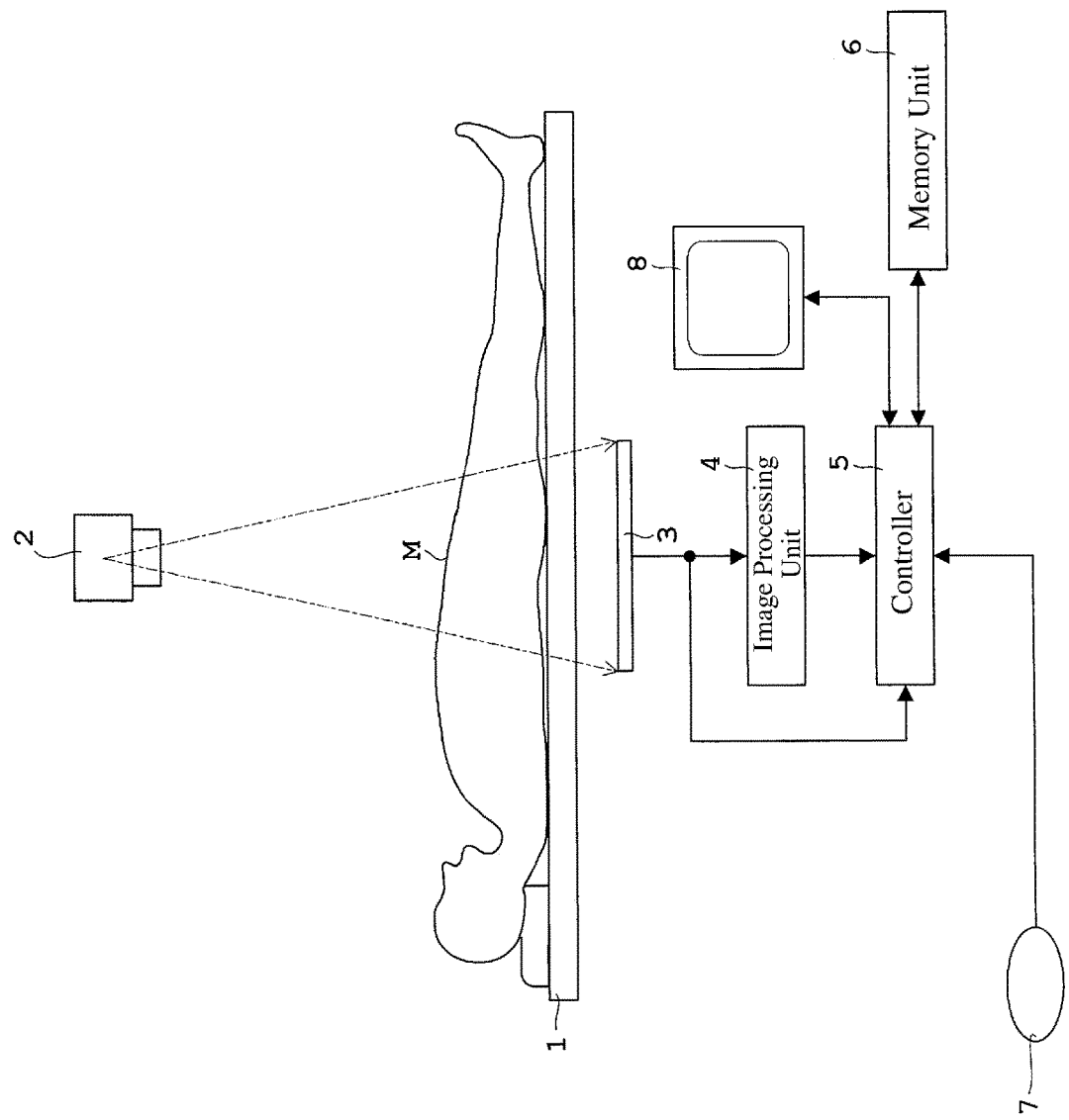
FIG. 1 is a block diagram of an X-ray imaging apparatus according to each example.
Figure 2:
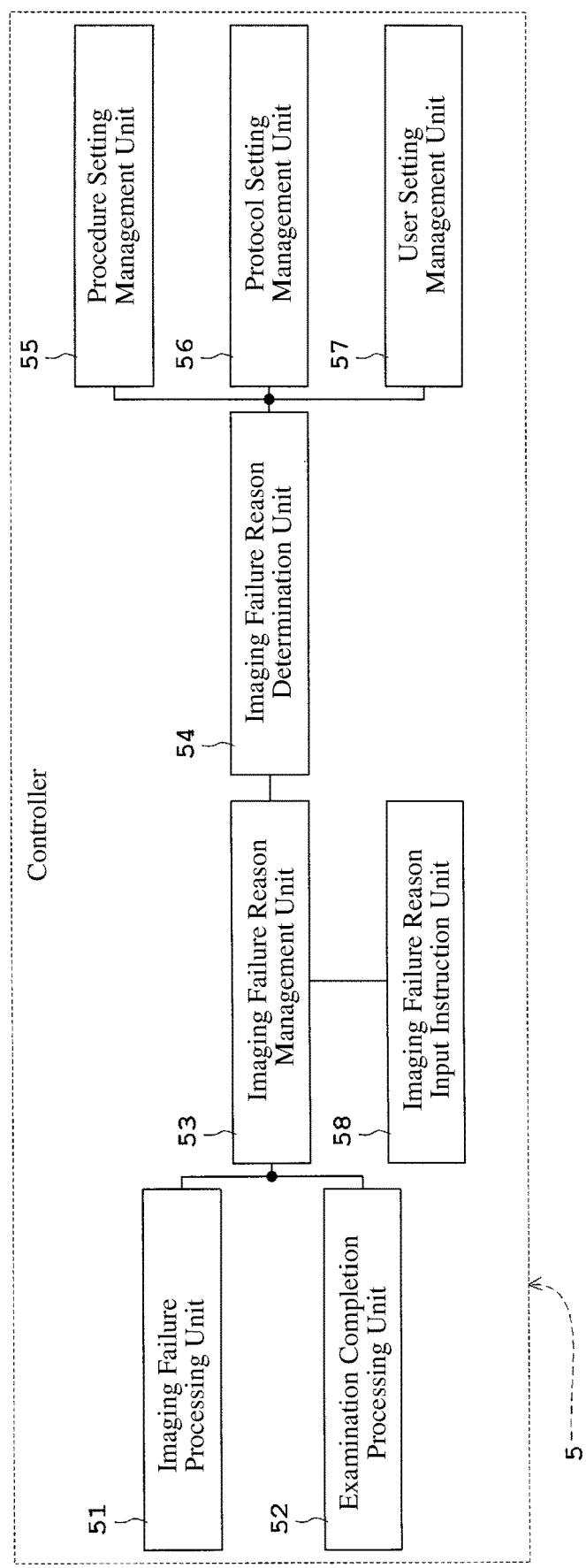
FIG. 2 is a block diagram regarding an imaging failure in a controller of the X-ray imaging apparatus according to each example.

FIG. 1 is a block diagram of an X-ray imaging apparatus according to each example. FIG. 2 is a block diagram related to an imaging failure at a controller of an X-ray imaging apparatus according to each example. FIG. 1 and FIG. 2 have the same configuration in each example.

As shown in FIG. 1, including Example 2 described later, the X-ray imaging apparatus according to this Example 1 is provided with a top board 1 on which a subject M who is a patient is placed, an X-ray tube 2 for emitting X-rays toward the subject M, and a flat-panel X-ray detector (hereinafter abbreviated as "FPD") 3 for detecting X-rays emitted from the X-ray tube 2 and transmitted through the subject M.

Other than the above, the X-ray imaging apparatus is provided with an image processing unit 4, a controller 5, a memory unit 6, an input unit 7, and a display unit 8. The image processing unit 4 performs image processing on an X-ray image based on X-rays detected by the FPD 3. The controller 5 collectively controls each constituent portion described later. The memory unit 6 stores an X-ray image before image processing acquired by the FPD 3 or an X-ray image acquired by various image processing with the image processing unit 4 via the controller 5. The memory unit 6 further stores a reason for a failure of imaging (imaging failure reason) which will be described later. The input unit 7 is configured for an operator such as a technician to input data and/or instructions (commands). The display unit 8 displays an X-ray image before image processing and an X-ray image after image processing by the image processing unit 4. The display unit 8 further displays a procedure edit screen 8A (see FIG. 3), a procedure edit screen 8B (see FIG. 4), an user information registration screen 8C (see FIG. 5), and an input dialogue of the imaging failure reason, which will be described later. The controller 5 (particularly the imaging failure reason determination unit 54 shown in FIG. 2 described later) corresponds to the necessity/unnecessity setting means and the display controller in the present invention. The input unit 7 corresponds to the necessity/unnecessity input means in the present invention.

The FPD 3 is configured by a plurality of detecting elements sensitive to X-rays arranged in a two-dimensional matrix on the detecting surface. The detecting element converts the X-rays transmitted through the subject M into an electric signal, temporarily accumulates the electric signal, and reads out the accumulated electric signal to detect the X-rays. Each of the detecting elements converts the detected electrical signal to a pixel value corresponding to the electrical signal and outputs an X-ray image by assigning the pixel value to each corresponding pixel at the position of the detecting element. The outputted X-ray image is sent to the image processing unit 4 or the memory unit 6 via the controller 5. As described above, in the FPD 3, the plurality of detecting elements for detecting X-rays is arranged in a matrix (two-dimensional matrix). The FPD 3 is used in an X-ray digital apparatus. The X-ray detector is not limited to an FPD and may be an X-ray detector used in an X-ray imaging analog apparatus such as an image intensifier (I.I).

The image processing unit 4 and the controller 5 are configured by a central processing unit (CPU) and the like. The image processing is, for example, offset correction, gradation conversion, grid removal, or the like. When the technician determines that the X-ray image acquired by the FPD 3 is an X-ray image that can be used for a diagnosis without subjecting it to the image processing by the image processing unit 4, the X-ray image is sent directly to the memory unit 6. To the contrary, when the technician determines that the image processing is necessary, the X-ray image is sent to the image processing unit 4. The image processing is performed by the image processing unit 4 and then sent to the memory unit 6. The specific functions of the controller 5 will be described in detail later.

The memory unit 6 is configured by a storage medium, such as, e.g., a ROM (Read-only Memory) and a RAM (Random-Access Memory). Including Example 2, which will be described later, in this Example 1, the memory unit 6 writes and stores the X-ray image (before image processing) acquired by the FPD 3 or the X-ray image after image processing by the image processing unit 4. The X-ray image is read out from the memory unit 6 as needed and sent to the display unit 8, a printer (not shown), or an image server (not shown). In addition, the memory unit 6 writes and stores the imaging failure reason input to the imaging failure reason input dialog of the display unit 8 and reads out the imaging failure reason as necessary to send it to the screen of the display unit 8.

The input unit 7 is configured by a pointing device exemplified by a mouse, a keyboard, a joystick, a trackball, a touch panel, or the like. In this Example 1, including Example 2, which will be described later, the input unit 7 is configured by the touch panel, so the display unit 8 also functions as the input unit 7. The specific functions of the input unit 7 (here, touch panel) will also be described in detail later.

The display unit 8 is configured by a touch panel, a monitor, a television, or the like. In this example, as described above, the display unit 8 also serves as a function of the input unit 7. The display unit 8 is configured by a touch panel. The specific display modes of the display unit 8 will also be described in detail later.

As shown in FIG. 2, the controller 5 (see also FIG. 1) is provided with an imaging failure processing unit 51, an examination completion processing unit 52, an imaging failure reason management unit 53, an imaging failure reason determination unit 54, a procedure setting management unit 55, a protocol setting management unit 56, a user setting management unit 57, and an imaging failure reason input instruction unit 58. The imaging failure reason determination unit 54 corresponds to the necessity/unnecessity setting means in the present invention.

When the "imaging failure" button displayed on the touch panel or the screen is pressed, the imaging failure processing unit 51 notifies the imaging failure reason management unit 53 of the pressing of the "imaging failure" button. Alternatively, when the "Completion of examination" button displayed on the touch panel or the screen is pressed, the examination completion processing unit 52 notifies the imaging failure reason management unit 53 of the pressing of the "Completion of examination" button.

When there exits an imaging failure image for which the imaging failure reason has not yet been input, the imaging failure reason management unit 53 inquires of the imaging failure reason determination unit 54 whether or not the input of the imaging failure reason is necessary.

The imaging failure reason determination unit 54 inquires of the procedure setting management unit 55, the protocol setting management unit 56, and the user setting management unit 57 and collects the set value of whether or not the input of the imaging failure reason is necessary. The imaging failure reason determination unit 54 determines whether or not the input of the imaging failure reason is necessary from the collected results and notifies the imaging failure reason management unit 53 of the determination. Note that the set value on whether or not the input of the imaging failure reason is necessary is set depending on the condition input by the input unit 7 (see FIG. 1) in the setting item (check box), which will be described later.

The imaging failure reason input instruction unit 58 notifies the user (operator) of the fact that the input of the imaging failure reason is necessary and instructs the user to input the imaging failure reason. Specifically, the input dialog (the screen displayed as "Please select the imaging failure reason" in FIG. 17) of the imaging failure reason is displayed on the touch panel or the screen. The user selects the corresponding imaging failure reason and then presses the "OK" button.

Figure 4:
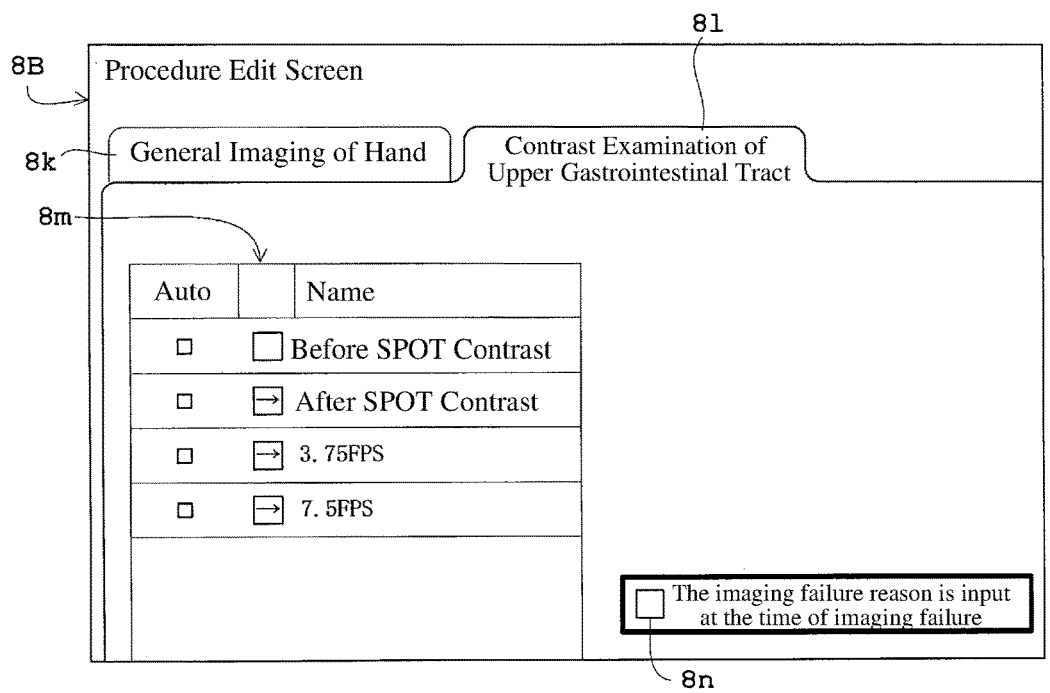
FIG. 4 is a display mode of a procedure edit screen according to Example 1.

Next, a display mode according to this Example 1 will be described with reference to FIG. 3 to FIG. 6. FIG. 3 is a display mode of the procedure edit screen according to Example 1. FIG. 4 is a display mode of the procedure edit screen according to Example 1. FIG. 5 is a display mode of the user information registration screen according to Example 1. (a) to (c) of FIG. 6 show circuit diagrams of the imaging failure reason determination unit when performing with the display modes of FIG. 3 and FIG. 5 combined.

First, a screen is displayed in which a setting item on whether or not "the imaging failure reason is input at the time of imaging failure" is added. The setting item is added, for example, for each imaging protocol as shown in FIG. 3, for each examination (procedure) as shown in FIG. 4, or for each user (operator) as shown in FIG. 5. In this Example 1, including Example 2, which will be described later, the setting item will be described by exemplifying a check box. When a check mark is present in the check box, the screen transits to a screen for inputting the imaging failure reason screen (input dialog of the imaging failure reason), and the imaging failure reason is selected and input. When a check mark is not present in the check box, the screen for inputting the imaging failure reason (input dialog of the imaging failure reason) is skipped.

In a state in which the check mark is present in the check box, when the check box or its description (in this instance, "the imaging failure reason is input at the time of imaging failure") is touched on the touch panel or clicked by a mouse, the check box is reversed, and the check mark will be removed from the check box. Conversely, in a state in which no check mark is preset in the check box, when the check box or its description (in this instance, "the imaging failure reason is input at the time of imaging failure") is touched on the touch panel or clicked by a mouse, the check box is reversed, and a check mark is put in the check box.

As shown in FIG. 3, the procedure edit screen 8A is activated. The procedure edit screen 8A includes tabs, for example, a "General" tab 8a, a "Fluoroscopy" tab 8b, and an "Imaging" tab 8c. FIG. 3 shows a display mode when the "Imaging" tab 8c is selected. When the "Imaging" tab 8c is selected, a plurality of imaging protocols is displayed. For example, an imaging protocol 8d of "Before SPOT contrast", an imaging protocol 8e of "After SPOT contrast", an imaging protocol 8f of "3.75 FPS", and an imaging protocol 8g of "7.5 FPS" are displayed.

Here, the "Before SPOT contrast" denotes imaging before administering a contrast agent in a local region of interest. The "After SPOT contrast" denotes imaging after administering a contrast agent in a local region of interest. The "3.75 FPS" denotes continuous imaging at the imaging speed of 3.75 frames per second. The "7.5 FPS" denotes continuous imaging at the imaging speed of 7.5 frames per second. Note that the imaging is performed in the order of "Before SPOT contrast", "After SPOT contrast", "3.75 FPS", and "7.5 FPS".

FIG. 3 shows a display mode when the imaging protocol 8d of "Before SPOT contrast" is selected. When the imaging protocol 8d of "Before SPOT contrast" is selected, tabs are provided on the right side. For example, an "X-ray/imaging conditions" tab 8h and a "Processing" tab 8i are provided. FIG. 3 shows a display mode when the "X-ray/imaging conditions" tab 8h is selected. When the "X-ray/imaging conditions" tab 8h is selected, X-ray conditions, imaging conditions, and the like are displayed. When the "Processing" tab 8i is selected, image processing conditions (image processing parameters), etc., by the image processing unit 4 (see FIG. 1) are displayed.

When the "X-ray/imaging conditions" tab 8h is selected after selecting the imaging protocol 8d of "Before SPOT contrast", a check box 8j for each imaging protocol is displayed. The "Before SPOT contrast" is imaging before administering a contrast agent, so there is a possibility that the imaging failure occurs. Therefore, when the imaging protocol 8d of "Before SPOT contrast" is selected, a check mark is put in the check box 8j, and the imaging failure reason at the time of imaging failure is input. In this manner, in the imaging protocol 8d of "Before SPOT contrast", the setting of whether or not the input of the imaging failure reason is necessary is performed.

Thereafter, in the same manner, the imaging protocol 8e of "After SPOT contrast" is selected, and the setting of whether or not the input of the imaging failure reason is necessary is performed in the imaging protocol 8e of "After SPOT contrast". The imaging protocol 8f of "3.75 FPS" is selected, and the setting of whether or not the input of the imaging failure reason is necessary is performed in the imaging protocol 8f of "3.75 FPS". The imaging protocol 8g of "7.5 FPS" is selected, and the setting of whether or not the input of the imaging failure reason is necessary is performed in the imaging protocol 8g of "7.5 FPS".

As shown in FIG. 4, the procedure edit screen 8B is activated. Like the procedure edit screen 8A of FIG. 3, the procedure edit screen 8B of FIG. 4 includes tabs. The tab is provided for each procedure in which a series of imaging is collectively performed. For example, a "General imaging of hand" tab 8k and a "Contrast examination of upper gastrointestinal tract" tab 8l are provided. FIG. 4 shows a display mode when the "Contrast examination of upper gastrointestinal tract" tab 8l is selected. When the "Contrast examination of upper gastrointestinal tract" tab 8l is selected, a plurality of imaging protocols (see symbol 8m in FIG. 4) is displayed in the same manner as in FIG. 3.

In the case of FIG. 3, the setting of whether or not the input of the imaging failure reason is necessary is performed for each imaging protocol. On the other hand, in the case of FIG. 4, the setting of whether or not the input of the imaging failure reason is necessary is performed for each procedure. In other words, when an imaging protocol belongs to the same procedure, the setting of whether or not the input of the imaging failure reason is necessary is collectively performed in each imaging protocol.

When the "Contrast examination of upper gastrointestinal tract" tab 8l is selected, the check box 8n is displayed for each procedure. Since the "Contrast examination of upper gastrointestinal tract" is contrast imaging, an input of imaging failure reason is unnecessary. Therefore, when the "Contrast examination of upper gastrointestinal tract" tab 8l is selected, the check mark is removed from the check box 8n to skip the screen (input dialog of the imaging failure reason) for inputting the imaging failure reason.

On the other hand, in the "General imaging of hand", the user's intention to input the imaging failure reason can be set. In the "General imaging of hand", when the user determines that the input of the imaging failure reason is necessary and selects the "General imaging of hand" tab 8k, a check mark is put in the check box 8n and the imaging failure reason at the time of the imaging failure is input. In the "General imaging of hand", when the user determines that the input of the imaging failure reason is unnecessary and selects the "General imaging of hand" tab 8k, the check mark is removed from the check box 8n to skip the screen (input dialog of the imaging failure reason) for inputting the imaging failure reason.

As shown in FIG. 5, the user information registration screen 8C is activated. The user information registration screen 8C has input items for inputting the user information and drop-down lists. For example, provided are a "Login name" input item 8o, a "Password" input item 8p, a "Password (Re-entry)" input item 8q, a "Group" drop-down list 8r, a "User attribution" drop-down list 8s, a "Kanji" input item 8t, and a "Roman character" input item 8u. On the lower side of the user information registration screen 8C, the check box 8v for each user is displayed.

In the "User attribution" drop-down list 8s, a doctor and a technician are listed, and the user selects one of them from the list. For example, when the user is a doctor, the user selects a "Doctor" from the list of the "User attribution" drop-down list 8s. When the user is a technician, the user selects a "Technician" from the list of "User attribution" drop-down list 8s.

As described above, when the user is a doctor, it is assumed that the user is not required to input the imaging failure reason. So, when the user selects a "Doctor" from the list in the "User attribution" drop-down list 8s, the check mark is removed from the check box 8v to skip the screen (input dialog for the imaging failure reason) for inputting the imaging failure reason. On the other hand, when the user is a technician, it is assumed that the user is required to input the imaging failure reason. So, when the user selects a "Technician" from the list of the "User attribution" drop-down list 8s, the check mark is put in the check box 8v to input the imaging failure reason at the time of imaging failure.

Note that it has been described that the user who does not need to input the imaging failure reason is a doctor and the user who needs to input the imaging failure reason is a technician. However, it may be set such that when the user is an experienced technician, the input of the imaging failure reason is unnecessary, and when the user is a less experienced technician, the input of the imaging failure reason is necessary. Therefore, when the user is an experienced technician, the check mark is removed from the check box 8v to skip the input dialog (input dialog of the imaging failure reason) for inputting the imaging failure reason. When the user is a less experienced technician, the user puts a check mark in the check box 8v to input the imaging failure reason at the time of imaging failure.

In accordance with the input operation to the check box 8j for each imaging protocol in FIG. 3, the set value on whether or not the input of the imaging failure reason is necessary is sent to the protocol setting management unit 56 shown in FIG. 2. In accordance with the input operation to the check box 8n for each procedure in FIG. 4, the set value on whether or not the input of the imaging failure reason is necessary is sent to the procedure setting management unit 55 shown in FIG. 2. In accordance with the input operation to the check box 8v for each user shown in FIG. 5, the set value on whether or not the input of the imaging failure reason is necessary is sent to the user setting management unit 57 shown in FIG. 2.

Note that the display modes of FIG. 3 to FIG. 5 may be implemented individually. Alternatively, the display modes of FIG. 3 to FIG. 5 may be implemented in combination. In particular, the check box 8*j* for each imaging protocol of FIG. 3 and the check box 8*v* for each user of FIG. 5 may be combined. Further, the check box 8*n* for each procedure of FIG. 4 and check box 8*v* for each user of FIG. 5 may be combined.

By combining them as described above, it is possible to set whether or not the input of the imaging failure reason is necessary according to the detailed cases, e.g., who performs the imaging or which imaging or examination (procedure) is executed. In the case of executing by combining them, when the setting of FIG. 3 and that of FIG. 5 conflict or when the setting of FIG. 4 and that of FIG. 5 conflict, there is no particular limitation as to which setting is to be prioritized, whether or not the logical AND of the setting items of both combinations are to be taken, or whether or not the logical sum thereof is to be taken. For example, when it is set that the input of the imaging failure reason is necessary, the set value on whether or not the input of the imaging failure reason is necessary is set to "1". When it is set that the input of the imaging failure reason is unnecessary, the set value on whether or not the input of the imaging failure reason is necessary is set to "0".

At this time, in cases where the controller 5 shown in FIG. 1 is configured by a programmable device (e.g., FPGA (Field Programmable Gate Array) in which the hardware circuit (e.g., a logic circuit) used internally can be changed in accordance with the program data, the imaging failure reason determination unit 54 shown in FIG. 2 may be configured by the circuit shown in FIG. 6.

In cases where either one of the set value (the set value on whether or not the input of the imaging failure reason is necessary by the input operation to the check box 8*j* for each imaging protocol in FIG.) from the protocol setting management unit 56 shown in FIG. 2 and the set value (the set value on whether or not the input of the imaging failure reason is necessary by the input operation to the check box 8*v* for each user) from the user setting management unit 57 shown in FIG. 2 is prioritized, the imaging failure reason determination unit 54 is configured by the selector switch 54*a* as shown in (a) of FIG. 6.

For example, when the "setting from the user information is prioritized" radio button and the "setting from the protocol information is prioritized" radio button are displayed on the screen and the "setting from the user information is prioritized" radio button is selected (pressed) using the input unit 7 (see FIG. 1), the selector switch 54*a* switches to the contact of the user setting management unit 57. When the "setting from the protocol information is prioritized" radio button is selected (pressed) using the input unit 7, the selector switch 54*a* switches to the contact point of the protocol setting management unit 56. The radio button is also called an "option button" and is used to select one of the predefined selections. When one button is selected (pressed), the button that was previously selected (pressed) returns to the non-selected (pressed) state, so only one button is always selected (pressed).

Note that the description will be omitted for the case in which either one of the set value 2 (the set value on whether or not the input of the imaging failure reason is necessary by the input operation to the check box 8*n* for each procedure in FIG. 4) from the procedure setting management unit 55 shown in FIG. 2 and the set value (the set value on whether or not the input of the imaging failure reason is necessary by the input operation to the check box 8*v* for each user in FIG. 5) from the user setting management unit 57 shown in FIG. 2 is prioritized.

In cases where the logical sum of the set value (the set value on whether or not the input of the imaging failure reason is necessary by the input operation to the check box 8*j* for each imaging protocol in FIG. 3) from the protocol setting management unit 56 shown in FIG. 2 and the set value (the set value on whether or not the input of the imaging failure reason is necessary by the input operation to the check box 8*v* for each user in FIG. 5) from the user setting management unit 57 shown in FIG. 2 is output, the imaging failure reason determination unit 54 is configured by the OR circuit 54*b* as shown in (b) of FIG. 6.

For example, when putting the check mark to the check box 8*j* for each imaging protocol in FIG. 3, the set value on whether or not the input of the imaging failure reason is necessary is "1". When putting the check mark to the check box 8*v* for each user in FIG. 5, the set value on whether or not the input of the imaging failure reason is necessary is "1". Therefore, when at least one of the two check boxes includes the check mark, the value of the logical sum output is "1" regardless of the state of the other remaining check box. Therefore, it is set that the input of the imaging failure reason is necessary. Only when both the check marks are removed from the two check boxes, the value of the logical sum becomes "0". Therefore, it is set that the input of the imaging failure reason is unnecessary.

Note that the description will be omitted for the case in which the logical sum of the set value (the set value on whether or not the input of the imaging failure reason is necessary by the input operation to the check box 8*n* for each procedure in FIG. 4) from the procedure setting management unit 55 shown in FIG. 2 and the set value (the set value on whether or not the input of the imaging failure reason is necessary by the input operation to the check box 8*v* for each user in FIG. 5) from the user setting management unit 57 shown in FIG. 2 is output.

In cases where the logical product of the set value (the set value on whether or not the input of the imaging failure reason is necessary by the input operation to the check box 8*j* for each imaging protocol in FIG. 3) from the protocol setting management unit 56 shown in FIG. 2 and the set value 2 (the set value on whether or not the input of the imaging failure reason is necessary by the input operation to the check box 8*v* for each user in FIG. 5) from the user setting management unit 57 shown in FIG. 5 is output, the imaging failure reason determination unit 54 is configured by the AND circuit 54*c* as shown in (c) of FIG. 6.

For example, when removing the check mark from the check box 8*j* for each imaging protocol in FIG. 3, the set value on whether or not the input of the imaging failure reason is necessary is "0". When removing the check mark from the check box 8*v* for each user in FIG. 5, the set value on whether or not the input of the imaging failure reason is necessary is "0". Therefore, when the check mark is removed from at least one of the two check boxes, the output value of the logical product becomes "0" regardless of the state of the other remaining check box. Therefore, it is set that the input of the imaging failure reason is unnecessary. Only when the check marks are put in both the check boxes, the output value of the logical product is "1". Therefore, it is set that the input of the imaging failure reason is necessary.

Note that the description will be omitted for the case in which when the logical product of the set value (the set value on whether or not the input of the imaging failure reason is necessary by the input operation to the check box 8*n* for each procedure in FIG. 4) from the procedure setting management unit 55 shown in FIG. 2 and the set value (the set value on whether or not the input of the imaging failure reason is necessary by the input operation to the check box 8v for each user in FIG. 5) from the user setting management unit 57 shown in FIG. 2 is output.

In the above description, when it is set that the input of the imaging failure reason is necessary, the set value on whether or not the input of the imaging failure reason is necessary is set to "1". When it is set that the input of the imaging failure reason is unnecessary, the set value on whether or not the input of the imaging failure reason is necessary is set to "0". However, the set value may be reversed. In other words, it may be configured as follows. When it is set that the input of the imaging failure reason is necessary, the set value on whether or not the input of the imaging failure reason is necessary is set to "0". When it is set that the input of the imaging failure reason is unnecessary, the set value on whether or not the input of the imaging failure reason is necessary is set to "1".

Further, in the case of performing a setting of whether or not the input of the imaging failure reason is necessary for each user, by dividing the imaging protocols used for the respective users in advance, the same effects as in the case of performing a setting of whether or not the input of the imaging failure reason is necessary for each imaging protocol can be obtained. Similarly, in the case of performing a setting of whether or not the input of the imaging failure reason is necessary for each user, by dividing the procedures used for the respective users in advance, the same effects as in the case of performing a setting of whether or not the input of the imaging failure reason is necessary for each procedure can be obtained.

Next, a series of imaging including a setting of whether or not the input of the imaging failure reason is necessary will be described with reference to FIG. 7, FIG. 16 and FIG. 17. FIG. 7 is a flowchart of a series of imaging according to Example 1 including a setting of whether or not the input of the imaging failure reason is necessary.

In FIG. 7, FIG. 16, and FIG. 17, at two timings, i.e., when the "Imaging failure" button is pressed or when the "Examination completion" button is pressed, the imaging failure reason determination unit 54 (see FIG. 2) determines whether or not the input of the imaging failure reason is necessary for the imaging failure image and prompts the input of the imaging failure reason when the input of the imaging failure reason is necessary. Note that the timing is not limited to the above. For example, it may be configured such that whether or not the input of the imaging failure reason is necessary is determined at the time of transmitting the image during the examination and that the input of the imaging failure reason is prompted when the input of the imaging failure reason is necessary.

Here, in a series of imaging, when the user is a doctor and in the case of the imaging protocol or procedure which is low in imaging failure, it is predicted that the input of the imaging failure reason is unnecessary, prior to the series of imaging. Therefore, it is preferable to collectively perform input operations (an operation of putting a check mark in the check box when the input of the imaging failure reason is necessary, and an operation of removing a check mark from a check box when the input of the imaging failure reason is unnecessary) to check boxes (the check box 8j for each imaging protocol in FIG. 3, the check box 8n for each procedure in FIG. 4, and the check box 8v for each user in FIG. 5) at the time prior to the series of imaging operations. By collectively performing the input operations to the check boxes at the time prior to the series of imaging operations, it is possible to omit the input operation to the check box for each imaging or each procedure.

Note that when an imaging failure occurred during continuous imaging, the series of images are treated as imaging failure images. Of course, when an imaging failure occurs in the middle of the continuous imaging and the frame considered to have caused the imaging failure can be identified, the images acquired before the frame may not be treated as imaging failure images and the images acquired after the frame may be treated as imaging failure images.

(Step S1) Input Operation to Check Box

First, prior to a series of imaging operations, the input operations to the check boxes (the check box 8j for each imaging protocol in FIG. 3, the check box 8n for each procedure in FIG. 4, and the check box 8v for each user in FIG. 5) are collectively performed. When the input of the imaging failure reason is necessary, the check mark is put in the check box. When the imaging failure reason is unnecessary, the check mark is removed from the check box.

Upon the input operation to the check box, the procedure setting management unit 55 (see FIG. 2), the protocol setting management unit 56 (see FIG. 2), and the user setting management unit 57 (see FIG. 2) output the set value on whether or not the input of the imaging failure reason is necessary. When an inquiry is made from the imaging failure reason determination unit 54 (see FIG. 2) to the procedure setting management unit 55, the protocol setting management unit 56, and the user setting management unit 57 in Step S6, which will be described later, the imaging failure reason determination unit 54 collects the set values on whether or not the input of the imaging failure reason is necessary.

(Step S2) Imaging

Imaging is performed according to the X-ray conditions (the tube current and the tube voltage of the X-ray tube, the exposure time) and imaging conditions at the imaging protocol.

As shown in FIG. 16, near the screen for displaying the captured X-ray image (at the lower side of the screen in FIG. 16), an "Imaging failure" button B is provided. When an imaging failure occurs, the user presses the "Imaging failure" button B to set (register) the X-ray image displayed at that time as an imaging failure image (see Step S5 described later). As described above, when an imaging failure occurred during the continuous imaging, not only the X-ray image displayed at that time but also a series of X-ray images are set (registered) as imaging failure images. In order to exclude the imaging failure image, it is possible to press the "Imaging failure" button B even when the user is a doctor.

(Step 3) is Imaging Failure Button Pressed?

The imaging failure processing unit 51 (see FIG. 2) determines whether or not the "imaging failure" button B is pressed. When the "Imaging failure" button B is pressed, the imaging failure processing unit 51 notifies the imaging failure reason management unit 53 (see FIG. 2) of the fact, and the process proceeds to Step S5. When the "Imaging failure" button B is not pressed, the process proceeds to Step S4.

(Step 4) Is Examination Completion Button Pressed?

When the "Imaging failure" button B is not pressed, the examination completion processing unit 52 (see FIG. 2) determines whether or not the "Examination completion" button is pressed. When the "Examination completion" button is pressed, the examination completion processing unit 52 notifies the imaging failure reason management unit 53 of the fact, and the process proceeds to Step 10. When the "Examination completion" button is not pressed, the process returns to Step 2 to continue imaging.

(Step 5) Imaging Failure Registration

When the "Imaging failure" button B is pressed, the X-ray image captured in Step S2 is registered (registered as an imaging failure) as an imaging failure image.

(Step 6) Is Check Mark Present?

The imaging failure reason management unit 53 queries the imaging failure reason determination unit 54 (see FIG. 2) whether an input of the imaging failure reason is necessary. In Step 1, the imaging failure reason determination unit 54 inquires the procedure setting management unit 55, the protocol setting management unit 56, and the user setting management unit 57 whether or not a check mark is present in a check box, and collects the set values on whether or not the input of the imaging failure reason is necessary.

When a check mark is present in the check box and the set value on whether or not the input of the imaging failure reason is necessary is "0" and when a check mark is not present in the check box and the set value on whether or not the input of the imaging failure reason is necessary is "0", it is determined that a check mark is present when the imaging failure reason determination unit 54 collects the set value "1", and it is determined that a check mark is not present when the imaging failure reason determination unit 54 collects the set value "0". When the imaging failure reason determination unit 54 determines that a check mark is present, the process proceeds to Step 7. When a check mark is not present (i.e., a check mark is removed from the check box), the process proceeds to Step 9.

(Step S7) Display of Input Dialog

When a check mark is present, the imaging failure reason determination unit 54 determines that an input of the imaging failure reason is necessary and notifies the imaging failure reason management unit 53 of the fact. When the input of the imaging failure reason is necessary, the imaging failure reason management unit 53 notifies the imaging failure reason instruction unit 58 (see FIG. 2) of the fact that the input of the imaging failure reason is necessary. The imaging failure reason instruction unit 58 notifies the user of the fact that the input of the imaging failure reason is necessary to instruct the user to input the imaging failure reason. More specifically, as shown in FIG. 17, a screen (an input dialog of the imaging failure reason) entitled "Please select the imaging failure reason" is displayed. When the input dialog of the imaging failure reason is displayed, the user inputs the imaging failure reason by selecting the corresponding imaging failure reason and then pressing the "OK" button in FIG. 17.

(Step S8) Is OK button Pressed?

The imaging failure reason management unit 53 determines whether or not the "OK" button is pressed. When the "OK" button is pressed, the process proceeds to Step S9. Note that when the "Cancel" button in FIG. 17 is pressed, the input dialog for the imaging failure reason button is temporarily closed, and the process proceeds to Step S9. As the case in which the "Cancel" button is pressed, a case is considered that the input of the imaging failure reason is not performed at that time for some reason. As a case in which the input of the imaging failure reason is not performed at that time for some reason, for example, there is a case that there is no time to input the imaging failure reason.

(Step S9) Re-Imaging

When the imaging failure button B is pressed, re-imaging is performed. Then, the process returns to Step S3, and the processes from Step S3 and subsequent steps are repeated.

(S10) is there any Imaging Failure Image F on which Imaging Failure Reason has not been Input?

When the "Examination completion" button is pressed, the imaging failure reason management unit 53 determines whether or not there is an imaging failure image for which imaging failure reason has not yet been input.

Originally, in cases where the input of the imaging failure reason is necessary, when the "OK" button in FIG. 17 is pressed in Step S8, the imaging failure reason at the time of the imaging failure is input. Therefore, there cannot be any imaging failure image for which the imaging failure reason has not yet been input. However, when the "Cancel" button of FIG. 17 is pressed in Step S8, since the input of the imaging failure reason was not performed, there may be an imaging failure image for which the imaging failure reason has not yet been input.

Therefore, when the imaging failure reason management unit 53 determines that there is an imaging failure image for which the imaging failure reason has not yet been inputted, the process proceeds to Step 11. On the other hand, when there is no imaging failure image for which an input of the imaging failure reason imaging has not yet been input, the process of FIG. 7 is terminated considering that a series of imaging including the setting of whether or not the input of the imaging failure reason is necessary is completed.

(S11) Is Check Mark Present?

When the "Cancel" button of FIG. 17 is pressed in Step S8 and the "Examination completion" button is pressed in Step S4 after the re-imaging of Step S9, it means that the re-imaging of Step S9 has already been completed and that the imaging failure reason has not yet been input for the imaging failure image.

Even when there is an imaging failure image for which the imaging failure reason has not yet been input, the imaging failure reason management unit 53 inquires of the imaging failure reason determination unit 54 whether or not the input of the imaging failure reason is necessary in the same manner as in Step 6. In the same manner as in Step S6, the imaging failure reason determination unit 54 queries the procedure setting management unit 55, the protocol setting management unit 56, and the user setting management unit 57 whether or not a check mark is present in the check box in Step S1. In this manner, even when there is an imaging failure image for which the imaging failure reason has not yet been input, the imaging failure reason determination unit 54 determines whether or not the check mark is present in the check box in the same manner as in Step S6. When the imaging failure reason determination unit 54 determines that the check mark is present, the process proceeds to Step 12.

However, when the check mark is not present (i.e., the check mark is removed from the check box), unlike in Step S6, the re-imaging in Step S9 has been completed, and the input of the imaging failure reason is unnecessary. Therefore, the process of FIG. 7 is terminated on the assumption that a series of imaging including the setting of whether or not the input of the imaging failure reason is necessary has been completed.

(Step S12) Display of Input Dialog

In the same manner as in Step 7, when a check mark is present, the imaging failure reason determination unit 54 determines that the input of the imaging failure reason is necessary and notifies the imaging failure reason management unit 53 of the fact. As a result, the input dialog of the imaging failure reason is displayed in the same manner as in Step 7.

(Step S13) Is OK button Pressed?

In the same manner as in Step S8, the imaging failure reason management unit 53 determines whether or not the "OK" button in FIG. 17 is pressed. However, when the "Cancel" button in FIG. 17 is pressed, unlike Step S8, Steps S12 and S13 wait by looping until the "OK" button is pressed. When the "OK" button is pressed, unlike Step S8, the re-imaging of Step S9 has already been completed and the input of the imaging failure reason has already been completed. Therefore, the process of FIG. 7 is terminated on the assumption that the series of imaging including the setting of whether or not the input of the imaging failure reason is necessary have been completed.

According to the X-ray imaging apparatus of this Example 1, the apparatus is provided with the imaging failure reason determination unit 54 of the controller 5 that performs the setting of whether or not the input of the imaging failure reason at the time of imaging failure is necessary. Further, the controller 5 performs the following control. When the imaging failure reason determination unit 54 sets that the input of the imaging failure reason is necessary, the controller 5 controls such that the screen (the input dialog of the imaging failure reason) for inputting the imaging failure reason is displayed. When it is set by the imaging failure reason determination unit 54 that the input of the imaging failure reason is unnecessary, the controller 5 controls such that the input of the imaging failure reason screen (the input dialog of the imaging failure reason) is skipped. Since the apparatus is provided with the imaging failure reason determination unit 54 and the controller 5 is provided with the display control function, the input operation is automatically skipped when the input of the imaging failure reason is unnecessary. As a result, it is unnecessary to cancel the input of the imaging failure reason when the input of the imaging failure reason is unnecessary, and the burden the user (operator) can be reduced.

In this Example 1, the input unit 7 is configured to input whether or not the input of the imaging failure reason is necessary. On the other hand, the controller 5 controls such that the setting item (the check box in FIGS. 3 to 5) on whether or not the input of the imaging failure reason is necessary is displayed on the screen. In the setting item (check box) displayed on the screen, when it is input by the input unit 7 that the input of the imaging failure reason is necessary (when the operation of putting a check mark in the check box is performed), the imaging failure reason determination unit 54 sets that the input of the imaging failure reason is necessary. With this, when it is input by the input unit 7 that the input of the imaging failure reason is necessary in the setting item (check box) displayed on the screen, the screen for inputting the imaging failure reason (the input dialog of the imaging failure reason) is displayed, and the imaging failure reason is input on the screen. On the other hand, when it is input by the input unit 7 that the input of the imaging failure reason is unnecessary in the setting item (check box) displayed on the screen by the input unit 7 (when the check mark is removed from the check box), the imaging failure reason determination unit 54 sets that the input of the imaging failure reason is unnecessary. With this, when it is input by the input unit 7 that the input of the imaging failure reason is unnecessary in the setting item (check box) displayed on the screen, the screen (the input dialog of the imaging failure reason) for inputting the imaging failure reason is skipped. Therefore, the input operation is automatically skipped when the input of the imaging failure reason is unnecessary.

EXAMPLE 2

Next, Example 2 of the present invention will be described with reference to the attached drawings.

FIG. 8 is a display mode of a procedure edit screen according to Example 2 when it is set that the input of the imaging failure reason is necessary in a particular imaging protocol. FIG. 9 is a display mode of a procedure edit screen according to Example 2 when it is set that the input of the imaging failure reason is unnecessary in a particular procedure. FIG. 10 is a display mode of a procedure edit screen according to Example 2 when it is set that the input of the imaging failure reason is necessary in a particular procedure. FIG. 11 is a display mode of a procedure edit screen according to Example 2 when it is set that the input of the imaging failure reason is unnecessary in a particular procedure. FIG. 12 is a display mode of a user information registration screen according to Example 2 prior to logging in. FIG. 13 is a display mode of a user information registration screen according to Example 2, which is different from the example in FIG. 12. FIG. 4 is a display mode of a user information registration screen according to Example 2 when it is set that the input of the imaging failure reason is necessary in the case of a specific operator. FIG. 15 is a display mode of a user information registration screen according to Example 2 when it is set that the input of the imaging failure reason is unnecessary in the case of a specific operator.

In Example 1 described above, when it is input by the input unit 7 (see FIG. 1) that the input of the imaging failure reason is necessary in the setting item (check box) displayed on the screen (when the operation of putting a check mark in a check box is performed), the imaging failure reason determination unit 54 (see FIG. 2) sets that the input of the imaging failure reason is necessary. When it is input by the input unit 7 that the input of the imaging failure reason is unnecessary in the setting item (check box) displayed on the screen (when the operation of removing a check mark from a check box is performed), the imaging failure reason determination unit 54 (see FIG. 2) sets that the input of the imaging failure reason is unnecessary.

On the other hand, in this Example 2, the input unit 7 is configured to input operating conditions, and the imaging failure reason determination unit 54 performs a setting of whether or not the input of the imaging failure reason is necessary in accordance with the operating conditions input by the input unit 7. Further, in this Example 2, when it is set by the imaging failure reason determination unit 54 that the input of the imaging failure reason is unnecessary in a specific operating condition, the controller 5 (see FIG. 1 and FIG. 2) controls such that the screen for performing the setting of whether or not the input of the imaging failure reason is necessary in the specific operating condition is skipped. The input unit 7 of this Example 2 corresponds to the operating condition input means in the present invention.

In this Example 2, the functions of the controller 5, the input unit 7, and the imaging failure reason determination unit 54 are different from those of Example 1 described above. Display modes according to this Example 2 will be described with reference to FIG. 8 to FIG. 15.

In Example 1 described above, a screen is displayed in which a setting item (check box) on whether or not "The imaging failure reason is input at the time of at imaging failure" is added. On the other hand, in this Example 2, when it is set that the input of the imaging failure reason is unnecessary in the specified operating condition, the screen for performing the setting of whether or not the input of the imaging failure reason is necessary (for example, a screen in which a setting item (check box) on whether or not "The imaging failure reason is input at the time of imaging failure" is added) is skipped.

As shown in FIG. 8 or FIG. 9, the procedure edit screen 8A is activated. In the same manner as in Example 1 of FIG. 3, the procedure edit screen 8A is provided with, for example, a "General" tab 8a, a "Fluoroscopy" tab 8b, and an "Imaging" tab 8c. In the same manner as in FIG. 3 of Example 1 described above, when the "Imaging" tab 8c is selected, for example, the imaging protocol 8d of "Before SPOT contrast", the imaging protocol 8e of "After SPOT contrast", the imaging protocol 8f of "3.75 FPS", and the imaging protocol 8g of "7.5 FPS" are displayed.

FIG. 8 shows a display mode when the imaging protocol 8d of "Before SPOT contrast" is selected. FIG. 9 shows a display mode when the imaging protocol 8e of "After SPOT contrast" is selected. Similar to FIG. 3 of Example 1 described above, when the imaging protocol 8d of "Before SPOT contrast" or the imaging protocol 8e of "After SPOT contrast" is selected, for example, the "X-ray/imaging conditions" tab 8h and the "Processing" tab 8i are provided on the right side.

As shown in FIG. 8, when the "X-ray/imaging conditions" tab 8h is selected after the imaging protocol 8d of "Before SPOT contrast" is selected, the check box 8j is displayed in the same manner as in FIG. 3 of Example 1 described above. As described above, the "Before SPOT contrast" is imaging before administering a contrast agent, so an imaging failure may occur. Therefore, when the imaging protocol 8d of "Before SPOT contrast" is selected, the check mark is put in the check box 8j, and the imaging failure reason at the time of the imaging failure is input. In this manner, in the imaging protocol 8d of "Before SPOT contrast", the setting of whether or not the input of the imaging failure reason is necessary is performed.

On the other hand, since the "After SPOT contrast" is contrast imaging, the input of the imaging failure reason is unnecessary. Therefore, as shown in FIG. 9, when the imaging protocol 8e of "After SPOT contrast" is selected, the check box 8j of FIG. 3 and FIG. 8 is in a non-displayed state, and the screen (the input dialog of the imaging failure reason) for inputting the imaging failure reason is automatically skipped.

In this manner, the imaging failure reason determination unit 54 (see FIG. 2) sets whether or not the input of the imaging failure reason is necessary in accordance with the content of each imaging protocol input in the input unit 7 (see FIG. 1). For example, when the imaging protocol 8d of "Before SPOT contrast" is selected, it is programmed such that a screen is displayed in which a check box 8j on whether or not "the imaging failure reason is input at the time of imaging failure" is added and the imaging failure reason is input by putting a check mark in the check box 8j. When the imaging protocol 8e of "After SPOT contrast" is selected, it is programmed such that the screen in which the check box 8j of FIG. 3 and FIG. 8 is added is skipped and the imaging failure reason is not to be input. Among theses, the imaging failure reason determination unit 54 executes the program on the necessity/unnecessity setting, and the controller 7 (see FIGS. 1 and 2) executes the program on the display control.

In FIG. 8, the check box 8j is displayed when the imaging protocol 8d of "Before SPOT contrast" is selected. However, the following display modes may be adopted. For example, it may be configured such that a state in which a check mark is present in a check box 8j is defined as an initial state (i.e., a default state), a screen (the input dialog of the imaging failure reason) for inputting the imaging failure reason may be skipped by removing the check mark from the check box 8j only when the input of the imaging failure reason is unnecessary. Further, it also may be configured such that when the imaging protocol 8d of "Before SPOT contrast" is selected, similarly to FIG. 9, the check box is made in a non-displayed state, the screen is shifted to a screen (the input dialog of the imaging failure reason) for inputting the imaging failure reason, and the imaging failure reason is selected and input.

As shown in FIG. 10 and FIG. 11, the start procedure edit screen 8B is activated. Similar to FIG. 4 of Example 1 described above, the procedure edit screen 8B includes, for example, a "General imaging of hand" tab 8k and a "Contrast examination of upper gastrointestinal tract" tab 8l. FIG. 10 shows a display mode when the "General imaging of hand" tab 8k is selected. FIG. 11 shows a display mode when the "Contrast examination of upper gastrointestinal tract" tab 8l is selected. In the same manner as in FIG. 4 of Example 1 described above, when each of the tabs 8k and 8l is selected, a plurality of imaging protocols (see symbol 8m in FIG. 10 and FIG. 11) are displayed.

In the same manner as in FIG. 4 of Example 1 described above, in the case of FIG. 10 and FIG. 11, the setting on whether or not the input of the imaging failure reason is necessary is performed for each procedure. In other words, when imaging protocols belong to the same procedure, the settings of whether or not the input of the imaging failure reason is necessary are collectively performed in each imaging protocol.

As shown in FIG. 10, when the "General imaging of hand" tab 8k is selected, the check box 8n is displayed in the same manner as in FIG. 4 of Example 1 described above. As described above, in the case of "General imaging of hand", it is possible to set any user's intention, e.g., the necessity of the input of the imaging failure reason. Therefore, in the case of "General imaging of hand", when the user determines that the input of the imaging failure reason is necessary and selects the "General imaging of hand" tab 8k, a check mark is put in the check box 8n and the imaging failure reason at the time of the imaging failure is input. In the case of "General imaging of hand", in cases where the user determines that the input of the imaging failure reason is unnecessary, when the user selects the "General imaging of hand" tab 8k, the check mark is removed from the check box 8n, and the screen (input dialog of the imaging failure reason) for inputting the imaging failure reason is skipped.

On the other hand, since the "Contrast examination of upper gastrointestinal tract" is contrast imaging, the input of the imaging failure reason is unnecessary. Therefore, as shown in FIG. 11, when the "Contrast examination of upper gastrointestinal tract" tab 8l is selected, the check box 8n in FIG. 4 and FIG. 10 is in a non-displayed state, and the screen (the input dialog of the imaging failure reason) for inputting the imaging failure reason is automatically skipped.

In this manner, the imaging failure reason determination unit 54 (see FIG. 2) performs the setting of whether or not the input of the imaging failure reason is necessary in accordance with the content of each procedure input in the input unit 7 (see FIG. 1). For example, when the "General imaging of hand" tab 8k is selected, It is programmed such that a screen in which a check box 8n is added is displayed and the imaging failure reason can be input by putting a check mark in the check box 8n and the imaging failure reason cannot be input by removing the check mark from the check box 8*n*. When the "Contrast examination of upper gastrointestinal tract" tab 8*l* is selected, it is programmed such that the screen in which the check box 8*n* of FIG. 4 and FIG. 10 is added is skipped to prevent the input of the imaging failure reason. Among these programmed programs, the imaging failure reason determination unit 54 executes the program related to the necessity/unnecessity setting, and the controller 7 (see FIGS. 1 and 2) executes the program related to the display control.

Although the check box 8*n* is displayed when the "General imaging of hand" tab 8*k* is selected in FIG. 10, the following display modes may be used in the same manner as in the modification of FIG. 8. For example, it may be configured such that the state in which the check mark is present in the box 8*n* is defined as an initial state (default state), and only when the input of the imaging failure reason is unnecessary, the check mark is removed from the check box 8*n* and the screen (the input dialog of the imaging failure reason) for inputting the imaging failure reason screen is skipped. Further, it may be configured such that when the "General imaging of hand" tab 8*k* is selected, similarly to FIG. 11, the check box becomes in a non-displayed state, the screen is shifted to a screen for inputting the imaging failure reason (the input dialog of the imaging failure reason), and the imaging failure reason is selected and input.

As shown in FIG. 12, the user information registration screen 8C is activated. In the same manner as in FIG. 5 of Example 1 described above, the user information registration screen 8C includes, for example, a "Login name" input item 8*o*, a "Password" input item 8*p*, and a "Password (Re-entry)" input item 8*q*. Unlike FIG. 5 of Example 1 described above, in FIG. 12 of this Example 2, the check box 8*v* of FIG. 5 is in the non-displayed state in the pre-login state. This is because, when a doctor logs in, it is obviously unnecessary to input the imaging failure reason, and therefore there is no problem even if the screen in which the check box 8*v* of FIG. 5 is added is skipped.

As described above, the imaging failure reason determination unit 54 (see FIG. 2) performs the setting of whether or not the input of the imaging failure reason is necessary in accordance with the information of each user (operator) input by the input unit 7 (see FIG. 1). Then, when it is set by the imaging failure reason determination unit 54 that the input of the imaging failure reason is unnecessary when the doctor logs in as a specific operator, the controller 7 (see FIG. 1 and FIG. 2) controls such that the setting screen (for example, a screen in which the setting item (check box) on whether or not "the imaging failure reason is input at the time of the imaging failure" is added) on whether or not the input of the imaging failure reason is necessary at the time of the specific operator (here, a doctor) is skipped.

In FIG. 12, the setting of whether or not the input of the imaging failure reason is necessary is performed in accordance with the information of the user who logs in. However, it may be configured to perform the setting of whether or not the input of the imaging failure reason is necessary in accordance with the user's information input in the display mode as shown in FIG. 13. For example, as shown in FIG. 13, when the user information registration screen 8C is activated, in the same manner as in FIG. 5 of Example 1 described above, the user information registration screen 8C includes, for example, a "User attribution" drop-down list 8*s*. In the same manner as in FIG. 5 of Example 1 described above, in the "User attribution" drop-down list 8*s*, a list of "Doctor" and "Technician" is displayed, and the user selects one of the relevant items from the list. In FIG. 13, in the same manner as in FIG. 12, the check box 8*v* in FIG. 5 is in a non-displayed state. When the user is a doctor, "Doctor" is selected from the list in the "User attribution" drop-down list 8*s*. When the user is a technician, a "Technician" is selected from the list in the "Use attribution" drop-down list 8.

When a technician logs in in FIG. 12, or when the "Technician" is selected from the list of the "User attribution" drop-down list 8*s* in FIG. 13, the display mode shifts to the display mode shown in FIG. 14. When the doctor logs in in FIG. 12 or selects the "Doctor" from the list of the "User attribution" drop-down list 8*s* in FIG. 13, the display mode shifts to the display mode shown in FIG. 15. As shown in FIG. 14 and FIG. 15, the user information registration screen 8C includes, for example, a "Kanji" input item 8*t* and a "Roman character" input item 8*u* in the same manner as in FIG. 5 of Example 1 described above.

In cases where the user is a technician, when an input is performed as shown in FIG. 12 or FIG. 13, a check box 8*v* is displayed on the lower side of the user information registration screen 8C as shown in FIG. 14. With this, the check box 8*v* for performing the setting of whether or not the input of the imaging failure reason is necessary in the case of a technician as a particular operator is displayed. As described above, when the user is an experienced technician, it is assumed that the input of the imaging failure reason is unnecessary, and the check mark is removed the from check box 8*v* to skip the screen for inputting the imaging failure reason (the input dialog of the imaging failure reason). On the other hand, when the user is a less experienced technician, the input of the imaging failure reason is necessary. Therefore, a check mark is put in the check box 8*v*, and the imaging failure reason is input at the time of imaging failure.

On the other hand, in cases where the user is a doctor, when an input is performed as shown in FIG. 12 or FIG. 13, in the user information registration screen 8C, the check box 8*v* as shown in FIG. 5 or FIG. 14 becomes in a non-displayed state as shown in FIG. 15, and the screen (the input dialog of the imaging failure reason) for inputting the imaging failure reason is automatically skipped. As a result, it is set that the input of the imaging failure reason is unnecessary in the case of a doctor as a specified operator.

As described above, the imaging failure reason determination unit 54 (see FIG. 2) performs the setting of whether or not the input of the imaging failure reason is necessary in accordance with the information of each user (operator) input by the input unit 7 (see FIG. 1). For example, in cases where the user is a technician, it is programmed such that the screen in which the check box 8*v* is added is displayed such that the imaging failure reason can be input in the check box 8*v* when a check mark is put in the check box 8*v* and the imaging failure reason cannot be input in the check box 8*v* when a check mark is removed from the check box 8*v*. When the user is a doctor, it is programmed such that the check box 8*v* shown in FIG. 5 and FIG. 14 is skipped so as not to input the imaging failure reason. Among these programmed programs, the imaging failure reason determination unit 54 executes the program related to the necessity/unnecessity setting, and the controller 7 (see FIG. 1 and FIG. 2) executes the program related to the display control.

Note that in FIG. 12 or FIG. 13, when the user inputs the "Technician", the check box 8*v* is displayed as shown in FIG. 14. However, the display mode may be as shown below in the same manner as in the modification of FIG. 8 or FIG. 10. For example, it may be configured such that the state in which the check mark is present in the check box 8*v* is defined as an initial state (default state), when the input of the imaging failure reason is unnecessary (for example, when the user is an experienced technician), the check mark is removed from the check box 8v to skip the screen (input dialog in imaging failure reason) for inputting the imaging failure reason. Further, when the user is a less experienced technician, it may be configured such that, for example, when the user logs in as shown in FIG. 12, the check box becomes in a non-displayed state in the same manner as in FIG. 15, and the screen (input dialog of the imaging failure reason) is shifted to a screen for inputting the imaging failure reason to select and input the imaging failure reason.

In the same manner as in Example 1 described above, it may be configured such that the display modes of FIG. 8 to FIG. 15 is displayed individually or the display modes of FIG. 8 to FIG. 15 is displayed in combination. In particular, it may be configured such that the check box 8j in the particular imaging protocol of FIG. 8 is implemented in combination with the check box 8v in the particular user (operator) of FIG. 14, or the check box 8n in the particular procedure of FIG. 10 is implemented in combination with the check box 8v in the particular user (operator) of FIG. 14. Specific combination methods (which setting is prioritized, whether the logical product of both the setting items is taken or the logical sum of both the setting items is taken) are omitted here because they have been described in FIG. 6 of Example 1 described above.

The flowchart of the series of imaging according to this Example 2 including the setting of whether or not the input of the imaging failure reason is necessary is the same as the flowchart of FIG. 7 of the above-described Example 1. Therefore, the explanation thereof is omitted. However, it should be noted that when the user is a doctor or in the case of the imaging protocol or the procedure with less imaging failure (i.e., when the input of the imaging failure reason is unnecessary), Step S1 (the input operation to the check box) of FIG. 7 is not performed in this Example 2.

In the same manner as in Example 1 described above, according to the X-ray imaging apparatus of this Example 2, the apparatus is provided with the imaging failure reason determination unit 54 of the controller 5 for performing the setting of whether or not the input of the imaging failure reason is necessary at the time of imaging failure. When it is set by the failing image determination unit 54 that the input of the imaging failure reason is necessary, the screen (the input dialog of the imaging failure reason) for inputting the imaging failure reason is displayed. When it is set by the failing image determination unit 54 that the input of the imaging failure reason is unnecessary, the controller 5 controls such that the screen (the input dialog of the imaging failure reason) for inputting the imaging failure reason is skipped. With this, the input operation is automatically skipped when the input of the imaging failure reason is unnecessary, thereby reducing the burden on the user (operator).

In this Example 2, the input unit 7 is configured to input operating conditions, and the imaging failure reason determination unit 54 performs the setting of whether or not the input of the imaging failure reason is necessary according to the operating conditions input by the input unit 7. On the other hand, when it is set by the imaging failure reason determination unit 54 that the input of the imaging failure reason is unnecessary in the specific operating condition, the controller 5 controls such that the screen (the screen in which setting items (check boxes) indicating whether or not "The imaging failure reason is input at imaging failure" is added) for performing the setting of whether or not the input of the imaging failure reason is necessary in the specific operating condition is skipped. With this, when the input of the imaging failure reason is unnecessary in a specific operating condition, the setting screen (the screen in which the check box is added) for performing the setting of whether or not the input of the imaging failure reason is necessary is skipped. Therefore, the operation of inputting that the input of the imaging failure reason is unnecessary is automatically skipped. As a result, in the case of the operating condition in which the input of the imaging failure reason becomes unnecessary, in addition to the operation of canceling the input of the imaging failure reason, the operation of inputting that the input of the imaging failure reason is unnecessary (the operation of removing the check mark from the check box) becomes unnecessary, which can reduce the burden on the user (operator).

Obviously, when the input of the imaging failure reason is unnecessary (for example, when the user is a doctor or when imaging with less imaging failure is performed), in Example 1 described above, it is only necessary to remove the check mark from the check box in order to set that the input of the imaging failure reason is unnecessary. However, when the number of imaging and the number of procedures increase, the operation of removing the check mark from the check box is performed each time, which results in troublesome operation. Therefore, in this Example 2, when the input of the imaging failure reason is unnecessary, the screen in which the check box is added is skipped (i.e., the check box is in a non-displayed state). Therefore, as compared with Example 1 described above, it becomes unnecessary to remove the check mark from the check box regardless of the number of images and the number of procedures.

When the operating condition input by the input unit 7 is the content of the imaging protocol, the imaging failure reason determination unit 54 sets whether or not the input of the imaging failure reason is necessary in accordance with the content of each imaging protocol input by the input unit 7. When it is set by the imaging failure reason determination unit 54 that the input of the imaging failure reason is unnecessary in the specific imaging protocol, the controller 5 controls such that the setting screen (the screen in which the check box is added) for performing a setting of whether or not the input of the imaging failure reason is necessary in the specific imaging protocol is skipped. With this, when the input of the imaging failure reason is unnecessary in a particular imaging protocol, the screen for performing the setting of whether or not the input of the imaging failure reason is necessary is skipped. Therefore, the operation of inputting that the input of the imaging failure reason is unnecessary is automatically skipped. As a result, in the case of the imaging protocol in which the input of the imaging failure reason is unnecessary (for example, "After SPOT contrast"), in addition to the operation of canceling the input of the imaging failure reason, the operation of inputting that the input of the imaging failure reason is unnecessary can be avoided, thereby further reducing the burden on the user (operator).

When the operating condition input by the input unit 7 is the content of a procedure in which a series of imaging is collectively performed, the imaging failure reason determination unit 54 performs the setting of whether or not the input of the imaging failure reason is necessary in accordance with the content of each procedure input by the input unit 7. When it is set by the imaging failure reason determination unit 54 that the input of the imaging failure reason is unnecessary in the specific procedure, the controller 5 controls such that the screen (the window in which the check box is added) for performing the setting of whether or not the input of the imaging failure reason is necessary in the specific procedure is skipped. As a result, when the input of the imaging failure reason is unnecessary in a particular procedure, the screen (the screen in which the check box is added) for performing the setting of whether or not the input of the imaging failure reason is necessary is skipped. Therefore, the operation for inputting that the input of the failing image reason is unnecessary is automatically skipped. As a result, in the case of the procedure in which the input of the imaging failure reason is unnecessary (for example, the "Contrast examination of upper gastrointestinal tract"), in addition to the operation of canceling the input of the imaging failure reason, the operation of inputting the input of the imaging failure reason is unnecessary is automatically skipped, which can further reduce the burden on the user (operator).

When the operating condition input by the input unit 7 is information of a user (operator), the imaging failure reason determination unit 54 performs the setting of whether or not the input of the imaging failure reason is necessary in accordance with the information of each user input by the input unit 7. When it is set by the imaging failure reason determination unit 54 that the input of the imaging failure reason is unnecessary in the case of a doctor as a specific operator, the controller 5 controls such that the screen (the window in which the check box is added) for performing the setting of whether or not the input of the imaging failure reason is necessary at the time of a specific operator (here, the doctor) is skipped. As a result, when the input of the imaging failure reason is unnecessary in the case of a particular operator (doctor), the screen (the screen in which the check box is added) for performing the setting of whether or not the input of the imaging failure reason is necessary is skipped. Therefore, the operation itself of inputting that the input of the imaging failure reason is unnecessary is automatically skipped. As a result, in the case of an operator in which the input of the imaging failure reason is unnecessary (for example, a doctor or an experienced technician), in addition to the operation of canceling the input of the imaging failure reason, the operation of inputting that the input of the imaging failure reason is unnecessary can be avoided, thereby further reducing the burden on the user (operator) can be further reduced.

It should be noted that the present invention is not limited to the above embodiments and can be modified as described below.

(1) As the X-ray imaging apparatus used in each Example described above, for example, a mobile X-ray imaging apparatus (round-trip vehicle) may be used, or a mounting type X-ray imaging apparatus may be used.

(2) In each Example described above (particularly Example 1), the check box is used as a setting term of whether or not the input of the imaging failure reason is necessary. However, the setting term is not limited to a check box. As long as it is a virtual tool (also called a "widget") in a graphical user interface (GUI: Graphical User Interface), for example, an icon, a drop-down list, a combo box, a radio button, or a tab, may be used. In the case of an icon, an icon indicating an input represented by a symbol and an icon indicating a skip of an input represented by a symbol are displayed on the screen. In the case of a drop-down list, for example, "the imaging failure reason is input at the time of imaging failure" or "the imaging failure reason is not input at the time of imaging failure" is displayed as a list, and the user selects one of them. In the case of a combo box, it is a combination of a drop-down list and text boxes, and it is possible to directly input the "The imaging failure reason is input at the time of imaging failure" or "The imaging failure reason is not input at the time of imaging failure" or it is possible to select one of them from the list. In the case of a radio button, for example, "The imaging failure reason is input at the time of imaging failure" button or a "The imaging failure reason is not input at the time of imaging failure" button are displayed on the screen, and one of these buttons is selected. In the case of a tab, in the same manner as in FIG. 3 and FIG. 4, for example, "The imaging failure reason is input at the time of imaging failure" tab or a "The imaging failure reason is not input at the time of imaging failure" tab is displayed on the screen, and the screen is switched to one of the tabs by selecting the tab.

(3) In Example 2 described above, the input unit 7 is configured to input operating conditions, and to perform the setting of whether or not the input of the imaging failure reason is necessary in accordance with the input operating condition, the setting of whether or not the input of the imaging failure reason is necessary is performed, for example, in accordance with the information of a user who logs in as shown in FIG. 12 or in accordance with the information of a user input as shown in FIG. 13. However, the present invention is not limited to such an embodiment. For example, it may be configured such that a bar code tag (IC tag) having user information may be read by a bar code reader, and the read user information is sent to the input/output port as an input means, and the setting of whether or not the input of the imaging failure reason is necessary is performed according to the sent user information. In this case, only by scanning the barcode tag (IC tag) worn by the doctor or the technician, the setting of whether or not the input of the imaging failure reason is necessary can be performed automatically.

DESCRIPTION OF SYMBOLS

5: Controller
54: Imaging failure reason determination unit
7: Input unit
8*j*, 8*n*, 8*v*: Check box

The invention claimed is:

1. An X-ray imaging apparatus for performing X-ray imaging, comprising:
    a necessity/unnecessity setting means configured to perform a setting of whether or not an input of an imaging failure reason at the time of an imaging failure is necessary, the imaging failure reason being a reason of a failure of imaging at the time of the imaging failure set as a failure of imaging; and
    a display controller configured to control such that a screen for inputting the imaging failure reason is displayed when it is set by the necessity/unnecessity setting means that the input of the imaging failure reason is necessary and that a screen for inputting the imaging failure reason is skipped when it is set by the necessity/unnecessity setting means that the input of the imaging failure reason is unnecessary.

2. The X-ray imaging apparatus as recited in claim 1, further comprising:
    a necessity/unnecessity input means configured to input whether or not the input of the imaging failure reason is necessary,
    wherein the display controller is configured to control such that a setting item on whether or not the input of the imaging failure reason is necessary is displayed on a screen,
    wherein when it is input by the necessity/unnecessity input means that the input of the imaging failure reason is necessary at the setting item displayed on the screen, the necessity/unnecessity setting means sets that the input of the imaging failure reason is necessary, and wherein when it is input by the necessity/unnecessity input means that the input of the imaging failure reason is unnecessary at the setting item displayed on the screen, the necessity/unnecessity setting means sets that the input of the imaging failure reason is unnecessary.

3. The X-ray imaging apparatus as recited in claim 1, further comprising:

an operating condition input means configured to input an operating condition, wherein the necessity/unnecessity setting means performs the setting of whether or not the input of the imaging failure reason is necessary depending on the operating condition input by the operating condition input means, and wherein when it is set by the necessity/unnecessity setting means that the input of the imaging failure reason is unnecessary in a specific operating condition, the display controller controls such that the screen for performing the setting of whether or not the imaging failure reason is necessary is skipped in the specific operating condition.

4. The X-ray imaging apparatus as recited in claim 3, wherein the operating condition to be input by the operating condition input means is a content of an imaging protocol, wherein the necessity/unnecessity setting means performs the setting of whether or not the input of the imaging failure reason is necessary depending on the content of each imaging protocol input by the operating condition input means, and wherein when it is set by the necessity/unnecessity setting means that the input of the imaging failure reason is unnecessary in a specific imaging protocol, the display controller controls such that the screen for performing the setting of whether or not the input of the imaging failure reason is necessary is skipped in the specific imaging protocol.

5. The X-ray imaging apparatus as recited in claim 3, wherein the operating condition to be input by the operating condition input means is information of an operator, wherein the necessity/unnecessity setting means performs the setting of whether or not the input of the imaging failure reason is necessary depending on the information of each operator input by the operating condition input means, and wherein when it is set by the necessity/unnecessity setting means that the input of the imaging failure reason is unnecessary in a case of a specific operator, the display controller controls such that the screen for performing the setting of whether or not the input of the imaging failure reason is necessary is skipped in the case of the specific operator.

6. The X-ray imaging apparatus as recited in claim 3, wherein the operating condition to be input by the operating condition input means is a content of a procedure in which a series of imaging is collectively performed, wherein the necessity/unnecessity setting means performs the setting of whether or not the input of the imaging failure reason is necessary depending on a content of each procedure input by the operating condition input means, and wherein when it is set by the necessity/unnecessity setting means that the input of the imaging failure reason is unnecessary in a specific procedure, the display controller controls such that the screen for performing the setting of whether or not the input of the imaging failure reason is necessary is skipped in the specific procedure.

* * * * *